United States Patent
Mei et al.

(10) Patent No.: US 9,493,542 B2
(45) Date of Patent: Nov. 15, 2016

(54) METHODS OF USING ERBB2 CONJUGATE PEPTIDES

(71) Applicant: Augusta University Research Institute, Inc., Augusta, GA (US)

(72) Inventors: Lin Mei, Evans, GA (US); Wen-Cheng Xiong, Evans, GA (US); Cheng-Yong Shen, Augusta, GA (US); Yan-Mei Tao, Martinez, GA (US); Shi-Wen Luo, Augusta, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 69 days.

(21) Appl. No.: 14/188,318

(22) Filed: Feb. 24, 2014

(65) Prior Publication Data

US 2014/0243268 A1    Aug. 28, 2014

Related U.S. Application Data

(60) Provisional application No. 61/768,333, filed on Feb. 22, 2013.

(51) Int. Cl.
| | | |
|---|---|---|
| A61K 38/16 | (2006.01) | |
| C07K 14/71 | (2006.01) | |
| C07K 7/08 | (2006.01) | |
| C07K 14/705 | (2006.01) | |
| A61K 47/48 | (2006.01) | |
| C07K 19/00 | (2006.01) | |
| A61K 38/00 | (2006.01) | |

(52) U.S. Cl.
CPC ......... *C07K 14/71* (2013.01); *A61K 47/48315* (2013.01); *C07K 7/08* (2013.01); *C07K 14/70596* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 7,595,151 B2* | 9/2009 | Lu | ........................... A61K 38/07 |
| 8,461,114 B2* | 6/2013 | Mei | ..................... C07K 14/4702 |
| 2004/0014055 A1* | 1/2004 | Birnbaum | ............ C07K 14/705 |

OTHER PUBLICATIONS

UniProtKB/Swis-Prot Database, Accession No. P04626, ERBB2_HUMAN, Dec. 9, 2015, Sequence updated Aug. 13, 1987, accessed Jan. 22, 2016.*
UniProtKB Database, Accession No. Q96RT1, LAP2_Human, version 2, Oct. 17, 2006, accessed Jan. 28, 2016.*
Anastasiadis, et al., "The p120 catenin family: complex roles in adhesion, signaling and cancer" , J Cell Sci., 113( Pt 8):1319-34 (2000).
Andrechek, et al, "Gene expression profiling of neu-induced mammary tumors from transgenic mice reveals genetic and morphological similarities to ErbB2-expressing human breast cancers" , Cancer Res., 63:4920-6 (2003).
Andrechek, et al., "Targeted disruption of ErbB2/Neu in the mammary epithelium results in impaired ductal outgrowth" , Oncogene , 24:932-7 (2005).

(Continued)

*Primary Examiner* — Claire Kaufman
(74) *Attorney, Agent, or Firm* — Pabst Patent Group LLP

(57) ABSTRACT

Compositions that inhibit or block the interaction between Erbin and ErbB2 and methods of their use are provided. Preferred compositions include peptides that inhibit or block Erbin and ErbB2 interaction under physiologic conditions in a subject. One embodiment provides an isolated peptide fragment of ErbB2 including the C-terminal 15 amino acids of ErbB2. The peptide fragment can be about 15 to 27 amino acids in length.

3 Claims, 19 Drawing Sheets

(56) References Cited

OTHER PUBLICATIONS

Apperson, et al., "Characterization of densin-180, a new brain-specific synaptic protein of the O-sialoglycoprotein family", J Neurosci., 16:6839-52 (1996).
Austin, et al., "Endocytosis and sorting of ErbB2 and the site of action of cancer therapeutics trastuzumab and geldanamycin", Mol. Biol. Cell, 15:5268-82 (2004).
Baulida, et al., "All ErbB receptors other than the epidermal growth factor receptor are endocytosis impaired", JBC, 271:5251-7 (1996).
Bentires-Alj, et al., "A role for the scaffolding adapter GAB2 in breast cancer", Nature Med., 12:114-21 (2006).
Berger, et al., "Correlation of c-erbB-2 gene amplification and protein expression in human breast carcinoma with nodal status and nuclear grading", Cancer Res, 48:1238-43 (1988).
Bilder and Perrimon, "Localization of apical epithelial determinants by the basolateral PDZ protein Scribble", Nature, 403:676-80 (2000).
Borg, et al., "ERBIN: a basolateral PDZ protein that interacts with the mammalian ERBB2/HER2 receptor", Nature Cell Biol., 2:407-14 (2000).
Boxus, et al., "The HTLV-1 Tax interactome", Retrovirology, 5:76 (2008).
Brantley-Sieders, et al, "The receptor tyrosine kinase EphA2 promotes mammary adenocarcinoma tumorigenesis and metastatic progression in mice by amplifying ErbB2 signaling", J Clinical Invest., 118:64-78 (2008).
Chazin, et al., "Transformation mediated by the human HER-2 gene independent of the epidermal growth factor receptor", Oncogene, 7:1859-66 (1992).
Cho, et al., "The rat brain postsynaptic density fraction contains a homolog of the *Drosophila* discs-large tumor suppressor protein", Neuron, 9 (5): 929-42 (1992).
Dai, et al., "Erbin inhibits transforming growth factor beta signaling through a novel Smad-interacting domain", Mole Cellular Biol.,7:6183-94 (2007).
Dai, et al., "Erbin inhibits RAF activation by disrupting the sur-8-Ras-Raf complex", JBC 281:927-33 (2006).
Dardousis, et al., "Identification of differentially expressed genes involved in the formation of multicellular tumor spheroids by HT-29 colon carcinoma cells", Mol Ther.,15:94-102 (2007).
Di Fiore, et al, "erbB-2 is a potent oncogene when overexpressed in NIH/3T3 cells", Science, 237:178-82 (1987).
Di Marco, et al, "Transformation of NIH 3T3 cells by overexpression of the normal coding sequence of the rat neu gene", Mole Cellular Biol., 10:3247-52 (1990).
Fantozzi, et al., "Mouse models of breast cancer metastasis", Breast Cancer Res., 8:212 (2006).
Guo, et al, "Beta 4 integrin amplifies ErbB2 signaling to promote mammary tumorigenesis", Cell, 126: 489-502 (2006).
Guy, et al., "Expression of the neu protooncogene in the mammary epithelium of transgenic mice induces metastatic disease", PNAS, 89:10578-82 (1992a).
Guy, et al., "Induction of mammary tumors by expression of polyomavirus middle T oncogene: a transgenic mouse model for metastatic disease", Mole Cellular Biol, 12:954-61 (1992b).
Hennighausen, et al., "Information networks in the mammary gland", Nature Rev., 6:715-25 (2005).
Huang, et al., "Erbin suppresses the MAP kinase pathway", JBC, 278:1108-14 (2003).
Huang, et al., "Erbin is a protein concentrated at postsynaptic membranes that interacts with PSD-9", JBC, 276:19318-26 (2001).
Hudziak, et al., "Increased expression of the putative growth factor receptor p185HER2 causes transformation and tumorigenesis of NIH 3T3 cells", PNAS, 84:7159-63 (1987).
Hynes, et al., "ErbB receptors and signaling pathways in cancer", Curr. Opin. Cell Biol., 21:177-84 (2009).
Johnson, et al, "HER2/ErbB2-induced breast cancer cell migration and invasion require p120 catenin activation of Rac1 and Cdc42", JBC, 285:29491-501 (2010).
Kao, et al., "RNA interference-based functional dissection of the 17q12 amplicon in breast cancer reveals contribution of coamplified genes", Genes, Chromosomes Cancer, 45:761-9 (2006).
Klapper, et al., Tumor-inhibitory antibodies to HER-2/ErbB-2 may act by recruiting c-Cbl and enhancing ubiquitination of HER-2 Cancer Res, 60:3384-8 (2000).
Kurokawa, et al., "ErbB (HER) receptors can abrogate antiestrogen action in human breast cancer by multiple signaling mechanisms", Clin. Cancer Res., 9:511S-5S (2000).
Lebeau, et al., "Comparative analysis of the expression of ERBIN and Erb-B2 in normal human skin and cutaneous carcinomas", Br. J. Dermatol., 152:1248-55 (2005).
Legouis, et al., "LET-413 is a basolateral protein required for the assembly of adherens junctions in Caenorhabditis elegans", Nature Cell Biol., 2:415-22 (2000).
Lenferink, et al., "Differential endocytic routing of homo- and hetero-dimeric ErbB tyrosine kinases confers signaling superiority to receptor heterodimers", EMBO J, 17:3385-97 (1998).
Leung, et al., "Outgrowth of single oncogene-expressing cells from suppressive epithelial environments", Nature, 482:410-3 (2012).
Li, et al, "Nuclear ErbB2 enhances translation and cell growth by activating transcription of ribosomal RNA genes.", Cancer Res., 71:4269-79 (2011).
Lu, et al., "14-3-3zeta Cooperates with ErbB2 to promote ductal carcinoma in situ progression to invasive breast cancer by inducing epithelial-mesenchymal transition", Cancer Cell, 16, 195-207 (2009).
Muller, et al, "Single-step induction of mammery adenocarcinoma in transgenic mice bearing the activated c-neu oncogene", Cell, 54:105-15 (1988).
Muthuswamy, et al., "ErbB2, but not ErbB1, reinitiates proliferation and induces luminal repopulation in epithelial acini", Nature Cell Biol., 3:785-92 (2001).
Nahta, et al., "Mechanisms of disease: understanding resistance to HER2- targeted therapy in human breast cancer", Nat Clin Pract Oncol., 3:269-80 (2006).
Neve, et al., "A collection of breast cancer cell lines for the study of functionally distinct cancer subtypes", Cancer Cell, 10:515-27 (2006).
Nofech-Mozes, et al., "Prognostic and predictive molecular markers in DCIS: a review", Adv Anat Pathol., 12:256-64 (2005).
Pan, et al., "Elevated expression of CUEDC2 protein confers endocrine resistance in breast cancer", Nature Med., 17:708-14 (2011).
Ponting, et al, "DHR domains in syntrophins, neuronal NO synthases and other intracellular proteins", Trends Biochem. Sci., 20 (3):102-3 (1995).
Ponting, "Evidence for PDZ domains in bacteria, yeast, and plants", Protein Sci., 6(2): 464-8 (1997).
Ranganathan, et al., "PDZ domain proteins: scaffolds for signaling complexes" Curr. Biol., 7 (12):R770-3 (1997).
Remmele, et al., "Immunohistochemical determination of estrogen and progesterone receptor content in human breast cancer. Computer-assisted image analysis (QIC score) vs. subjective grading (IRS)", Pathol. Res. Pract., 189:, 862-6 (1993).
Revillion, et al., "ERBB2 oncogene in human breast cancer and its clinical significance", Eur J Cancer, 34:791-808 (1998).
Rohan, et al., "Immunohistochemical detection of c-erbB-2 and p53 in benign breast disease and breast cancer risk", J Natl Cancer Inst., 90:1262-9 (1998).
Ross, et al., "Targeted therapy in breast cancer: the HER-2/neu gene and protein", Mol Cell Proteomics, 3:379-98 (2004).
Ross, et al., "The HER-2/neu oncogene in breast cancer: prognostic factor, predictive factor, and target for therapy", Stem cells, 16:413-28 (1998).
Rowse, et al., "Genetic modulation of neu proto-oncogene-induced mammary tumorigenesis", Cancer Res., 58: 2675-9 (1998).
Samanta, et al., "Ligand and p185c-neu density govern receptor interactions and tyrosine kinase activation", PNAS, 91:1711-5 (1994).
Schechter, et al, "The neu oncogene: an erb-B-related gene encoding a 185,000-Mr tumour antigen", Nature, 312:513-6 (1981).

(56) References Cited

OTHER PUBLICATIONS

Seton-Rogers, et al, "Cooperation, of the ErbB2 receptor and transforming growth factor beta in induction of migration and invasion in mammary epithelial cells", PNAS, 101: 1257-62 (2004).

Shelly, et al., "Polar expression of Erb8-2/HER2 in epithelia. Bimodal regulation by Lin-7", Developmental Cell, 5:475-86 (2003).

Shih, et al., "Transforming genes of carcinomas neuroblastomas introduced into mouse fibroblasts", Nature, 290:261-4 (1981).

Siegel, et al., "Elevated expression of activated forms of Neu/ErbB-2 and ErbB-3 are involved in the induction of mammary tumors in transgenic mice: implications for human breast cancer", EMBO J, 18:2149-64 (1999).

Slamon, et al, "Human breast cancer: correlation of relapse and survival with amplification of the HER-2/neu oncogene", Science, 235:177-82 (1987).

Slamon, et al., "Studies of the HER-2/neu proto-oncogene in human breast and ovarian cancer", Science, 244:707-12 (1989).

Sorkin, et al., "Endocytosis and intracellular trafficking of ErbBs", Exp. Cell Res., 314:3093-106 (2008).

Tao, et al., "Erbin regulates NRG1 signaling and myelination", PNAS, 106, 9477-82 (2009).

Tzahar, et al, "A hierarchical network of interreceptor interactions determines signal transduction by Neu differentiation factor/neuregulin and epidermal growth factor", Mole Cellular Biol, 16:5276-87 (1996).

Tzahar, et al, "ErbB-3 and ErbB-4 function as the respective low and high affinity receptors of all Neu differentiation factor/heregulin isoforms", JBC, 269:25226-33 (1994).

Van De Vijver, et al., "Neu-protein overexpression in breast cancer. Association with comedo-type ductal carcinoma in situ and limited prognostic value in stage II breast cancer", NEJM, 319:1239-45 (1988).

Waterman, et al., "Alternative intracellular routing of ErbB receptors may determine signaling potency", JBC, 273:13819-27 (1998).

Worthylake, et al., "ErbB-2 amplification inhibits down-regulation and induces constitutive activation of both ErbB-2 and epidermal growth factor receptors", JBC, 274, 8865-74 (1999).

Worzfeld, et al, "ErbB-2 signals through Plexin-B1 to promote breast cancer metastasis", J Clinical Invest., 122:1296-305 (2012).

Xu, et al., "Loss of Hsp90 association up-regulates Src-dependent ErbB2 activity", Mole Cellular Biol, 27:220-8 (2007).

Xu, et al., "Chaperone-dependent E3 ubiquitin ligase CHIP mediates a degradative pathway for c-ErbB2/Neu", PNAS, 99:12847-52 (2002a).

Xu, et al., "Hsp90, not Grp94, regulates the intracellular trafficking and stability of nascent ErbB2", Cell stress & chaperones, 7:91-6 (2002b).

Xu, et al., "Sensitivity of mature Erbb2 to geldanamycin is conferred by its kinase domain and is mediated by the chaperone protein Hsp90", JBC, 276:3702-8 (2001).

Yarden, et al., "The ERBB network: at last, cancer therapy meets systems biology", Nat Rev Cancer, 12:553-63 (2012).

Yu and Hung, "Overexpression of ErbB2 in cancer and ErbB2-targeting strategies", Oncogene, 19:6115-21 (2000).

Zaineddin, et al., "Serum enterolactone and postmenopausal breast cancer risk by estrogen, progesterone and herceptin 2 receptor status", Intl J Cancer, 130:1401-10 (2012).

Zhou, et al., ErbB2 degradation mediated by the co-chaperone protein CHIP JBC, 278:13829-37 (2003).

\* cited by examiner

METHODS OF USING ERBB2 CONJUGATE PEPTIDES

CROSS-REFERENCE TO RELATED APPLICATIONS

This application claims the benefit of and priority to U.S. Provisional Application No. 61/768,333, filed Feb. 22, 2013.

FIELD OF THE INVENTION

Aspects of the invention are generally directed to peptides, particularly ERB2 peptides.

REFERENCE TO SEQUENCE LISTING

The Sequence Listing submitted Feb. 24, 2014 as a text file named "GRU_2013_014_ST25.txt," created on May 6, 2016, and having a size of 4,761 bytes is hereby incorporated by reference pursuant to 37 C.F.R. §1.52(e)(5).

BACKGROUND OF THE INVENTION

Breast cancer is one of the most common cancers among women and is the second leading cause of cancer death in women. In 2012, approximately 290,000 new cases of breast cancer were predicted to be diagnosed, and approximately 40,000 women were predicted to die from breast cancer. ErbB2, also known as Her2, is overexpressed in >25% of breast cancers. Patients with ErbB2-overexpressing breast tumors show high recurrence, malignant metastasis, and poor prognosis (Berger, et al., *Cancer Res*, 48:1238-1243, 1988; Nahta, et al., *Nature Clinical Practice*, 3:269-280, 2006; Revillion, et al., *Eur J Cancer*, 34:791-808, 1998; Rohan, et al., *Journal of the National Cancer Institute*, 90:1262-1269, 1998; Ross, et al., *Stem cells*, 16:413-428, 1998; Slamon, et al, *Science*, 235:177-182, 1987; Slamon, et al., *Science*, 244:707-712, 1989; Yu, et al., *Oncogene*, 19:6115-6121, 2000).

Because of its critical role in breast tumor growth and progression, ErbB2 has been a target of therapeutic intervention for ErbB2-overexpressing mammary tumors (Nahta, et al., *Nature clinical practice*, 3:269-280, 2006; Ross, et al., *Mol Cell Proteomics*, 3:379-398, 2004; Yu, et al., *Oncogene*, 19:6115-6121, 2000). Effective drugs include trastuzumab and pertuzumab, humanized antibodies directed against the extracellular domain of ErbB2 and lapatinib, an inhibitor of EGFR and ErbB2. However, cancer cells often escape from trastuzumab or lapatinib treatment via intrinsic or de novo pathways (Nahta, et al., *Nature clinical practice*, 3:269-280, 2006). For example, ErbB2-positive breast tumors may become resistant to trastuzumab, or other antibody therapies, by alternative splicing or by proteolytic cleavage that generate p95HER2, a truncated form of ErbB2, or the extracellular ErbB2 is masked by the membrane-associated glycoprotein mucin-4 (MUC4). Thus, finding alternative treatment approaches is necessary.

Therefore, it is an object of the invention to provide methods and compositions for treating ErbB2-dependent breast cancer.

It is an object of the invention to provide methods and compositions for blocking, inhibiting or reducing the interaction of Erbin and ErbB2.

SUMMARY OF THE INVENTION

Compositions that inhibit or block the interaction between Erbin and ErbB2 and methods of their use are provided. Preferred compositions include peptides that inhibit or block Erbin and ErbB2 interaction under physiologic conditions in a subject. One embodiment provides an isolated peptide fragment of ErbB2 including the C-terminal 15 amino acids of ErbB2. The peptide fragment can be about 15 to 27 amino acids in length. A preferred peptide is PTAENPEYLGLDVPV (SEQ ID NO:1).

Conjugates and fusion proteins of the peptide are also provided. In one embodiment the ErbB2 peptide is linked or fused to a cell penetrating peptide including, but not limited to TAT. An exemplary fusion protein or conjugate is YGRKKRRQRRR-G-PTAENPEYLGLDVPV (SEQ ID NO:2).

The disclosed peptides, conjugates, and fusion proteins can be used to treat one or more symptoms of ErbB2-associated cancer including administering to a subject in need thereof an effective amount of the disclosed peptides, conjugates and fusion proteins. A preferred cancer to be treated is breast cancer.

Another embodiment provides a method of inhibiting Erbin and ErbB2 interaction by administering and effective amount of the disclosed peptides, conjugates, and fusion proteins to a cell.

A method of decreasing ErbB2-dependent growth of cancer cells is also provided. The method includes administering to a subject in need thereof an effective amount of a disclosed peptides, conjugates, or fusion proteins.

DETAILED DESCRIPTION OF THE INVENTION

I. Definitions

Figure 1A:
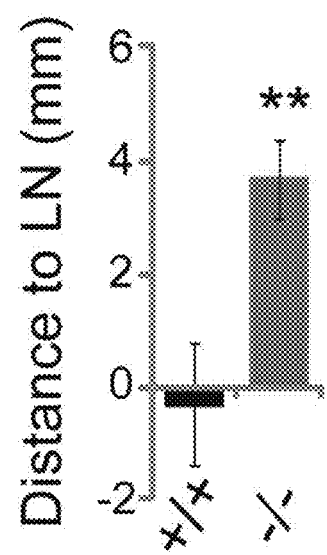
FIGS. 1A-1D show Erbin is expressed in luminal epithelial cells and is required for early mammary duct elongation and branching. (A) Increased distance between duct tips and lymph node in erbin$^{-/-}$ mice. Distance between duct tips and lymph nodes in #4 mammary glands were measured at 4-week-old mice. Ducts passing the lymph node were calculated as minus. n=4. P<0.01, compared to wild type littermates. (B) Reduced TEB area in erbin$^{-/-}$ mammary glands. Areas of 24 TEBs of 4 mammary glands of each genotype were measured. Shown were data for both front and side tips because front tips are larger than side ones in wild type. Notice different scale in Y-axis between side and front tips. P<0.01, compared to wild type littermates. (C) Reduced mammary gland coverage in fat pads during development. Data shown were for #3 and #4 mammary glands. n=3, P<0.01, compared to wild type littermates. (D) Reduced duct branches during development. n=3, P<0.01, compared to wild type littermates.

A "fusion protein" refers to a chimeric peptide, chimeric polypeptide, chimeric protein or chimeric peptide mimetic created through the joining of two or more genes which originally coded for separate proteins. Translation of this fusion gene results in a single polypeptide with functional properties derived from each of the original proteins. Fusion proteins can be prepared using conventional techniques in molecular biology.

As used herein, "treat" means to prevent, reduce, decrease, or ameliorate one or more symptoms, or characteristics of a musculoskeletal disease and disorder, particular an age-related musculoskeletal diseases and disorders.

The terms "individual," "subject," and "patient" are used interchangeably herein, and refer to a mammal, including, but not limited to, rodents, simians, and humans.

The terms "reduce", "inhibit", "alleviate" and "decrease" are used relative to a control. One of skill in the art would readily identify the appropriate control to use for each experiment. For example a decreased response in a subject or cell treated with a compound is compared to a response in subject or cell that is not treated with the compound.

As used herein, the terms "inhibitors" or "antagonists" refers to compounds or compositions that directly or indirectly partially or totally block activity, decrease, prevent, delay activation, inactivate, desensitize, or down regulate the activity or expression of the targeted molecule. Antagonists are, for example, polypeptides, such as antibodies, as well as nucleic acids such as siRNA or antisense RNA, as well as naturally occurring and synthetic antagonists, including small chemical molecules.

As used herein, the term "polypeptide" refers to a chain of amino acids of any length, regardless of modification (e.g., phosphorylation or glycosylation). The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

II. Compositions that Interfere with Erbin-ErbB2 Interaction

Exemplary compositions that interfere with Erbin-ErbB2 interaction include peptides containing fragments of Erbin or fragments of ErbB2. The peptides are preferably fragments that associate with Erbin thereby inhibiting the association of ErbB2 with Erbin. An exemplary ErbB2 peptide binds the PDZ domain of Erbin and has the following amino acid sequence PTAENPEYLGLDVPV (SEQ ID NO: 1) i.e., the carboxy terminal 15 amino acids of ErbB2.

The peptides include non-naturally occurring peptides and mimetics. The peptides can be any amino acid sequence that is identical to the entire sequence or a fragment of the ErbB2 binding domain of Erbin or the Erbin binding domain of ErbB2. The peptides can also include peptides that are not identical to the ErbB2 binding domain of Erbin or the Erbin binding domain of ErbB2 but mimic a particular sequence or the entire sequence of these domains. For example, the disclosed peptides can mimic the PDZ domain of Erbin.

The peptides can vary in length. The peptides can be 5, 10, 15, 20, 25, 30, 35, 40, 45, 50 or 100 amino acids in length. Typically peptides will be in the range of 5-200 amino acids in length.

A. ErbB2

The human epidermal growth factor receptor (HER) family of receptor tyrosine kinases, including epidermal growth factor receptor (EGFR) (HER1, ErbB1), ErbB2 (HER2, neu), ErbB3 (HER3), and ErbB4 (HER4), has been implicated in tumor growth and progression (Hynes, et al., *Curr. Opin. Cell Biol.*, 21:177-184, 2009; Yarden, et al., *Nat. Rev. Cancer,* 12:553-563, 2012; Yu, et al., *Oncogene,* 19:6115-6121, 2000). ErbB2, in particular, is overexpressed in >25% of breast cancers conferring high recurrence, malignant metastasis, and poor prognosis (Berger, et al., *Cancer Res,* 48:1238-1243, 1988; Revillion, et al., *Eur J Cancer,* 34:791-808, 1998; Rohan, *Journal of the National Cancer Institute,* 90:1262-1269, 1998; Ross, *Stem cells,* 16:413-428, 1998; Slamon, et al., *Science,* 235:177-182, 1987; Nahta, et al., *Nature clinical practice,* 3:269-280, 2006; Yu, et al., *Oncogene,* 19:6115-6121, 2000) and implicated in ovarian, stomach, and uterine tumors (Slamon, et al., *Science,* 244:707-712, 1989; Yarden, et al., *Nat Rev Cancer,* 12:553-563, 2012). ErbB2, originally identified as a transforming oncogene in a carcinogen-induced neuroblastoma (neu) (Shih, et al., *Nature,* 290:261-264, 1981), a homologue of HER (HER2), and as an oncogene of avian erythroblastosis virus (ErbB2), does not bind to ligand. However, it is a preferred heterodimerization partner of other ErbB receptors: EGFR, ErbB3 and ErbB4, in response to stimulation of EGF or heregulin/neuregulin, which increases dramatically the activity of dimerized partners (Tzahar, et al, *The Journal of biological chemistry,* 269:25226-25233, 1994; Tzahar, et al, *Molecular and cellular biology,* 16:5276-5287, 1996). Moreover, when overexpressed in breast tumor cells, ErbB2 forms ligand-independent hetero- or homodimers, which leads to cis- or transphosphorylation of the receptor complex (Di Fiore, et al, *Science,* 237:178-182, 1987; Di Marco, et al, *Molecular and cellular biology,* 10:3247-3252, 1990; Muthuswamy, et al, *Nature cell biology,* 2001; Samanta, et al, *Proceedings of the National Academy of Sciences of the United States of America,* 91:1711-1715, 1994; Worthylake, et al., *The Journal of biological chemistry,* 274:8865-8874, 1999). ErbB2 activation stimulates a plethora of downstream signaling pathways including Ras, Src, phosphoinositide 3-kinase (PI3K)/AKT, GAB2, and small G proteins, which eventually promote cancer cell proliferation, survival, epithelial-mesenchymal transition, migration and basement membrane invasion (Bentires-Alj, et al., *Nature medicine,* 12:114-121, 2006; Hynes, et al., *Curr. Opin. Cell Biol.,* 21:177-184, 2009; Johnson, et al, *The Journal of biological chemistry,* 285:29491-29501, 2010: Kurokawa, et al. *Clin. Cancer Res.,* 9:511S-515S, 2003; Lu, et al, *Cancer cell,* 16:195-207 2009; 2006; Seton-Rogers, et al, *Proceedings of the National Academy of Sciences of the United States of America,* 101: 1257-1262, 2004; Yarden, et al., *Nat. Rev. Cancer,* 12: 553-563, 2012; Yu, et al., *Oncogene* 19:6115-6121, 2000; Zhang, et al, *Nature medicine,* 17: 461-469, 2011). Signaling pathways that contribute to ErbB2 promotion of breast tumor development and/or metastasis including 14-3-3ζ, integrins, EphA2, CXCR4, and plexin-B1 have been identified (Brantley-Sieders, et al, *The Journal of clinical investigation,* 118:64-78; Guo, et al, *Cell* 126: 489-502, 2006; Li, et al, *Cancer Res.,* 71:4269-4279, 2011; Lu, et al, *Cancer cell,* 16:195-207, 2009; Worzfeld, et al, *Journal of clinical investigation,* 122:1296-1305, 2012).

In vitro and in vivo data support that ErbB2 has transforming potential. ErbB2 overexpression is able to transform mouse fibroblasts (NIH3T3 or NR6) and induces tumorigenic growth (Chazin, et al., *Oncogene,* 7:1859-1866, 1992: Di Fiore, et al, *Science,* 237:178-182, 1987; Hudziak, et al., *Proceedings of the National Academy of Sciences of the United States of America,* 84:7159-7163, 1987; Schechter, et al, *Nature,* 312:513-516, 1981). Overexpression of ErbB2 in estrogen receptor (ER)-expressing breast cancer cells confers estrogen-dependent, tamoxifen resistant tumorigenic growth (Benz et al, 1992). Moreover, overexpression of ErbB2 is sufficient to induce proliferation of MCF-10A cells, a normal human epithelial cell line, which form solid multiacinar structures resembling ductal carcinoma in situ (DCIS), an early stage of breast tumors (Leung, et al., *Nature,* 482:410-413, 2012; Muthuswamy, et al, *Nature cell biology,* 3:785-792, 2001). In transgenic mice, overexpression of ErbB2 or its activated form in mammary epithelium induces diffuse epithelial hyperplasia, mammary tumors, and lung metastases (Guy, et al, *Proceedings of the National Academy of Sciences of the United States of America,* 89:10578-10582, 1992; Muller, et al, *Cell,* 54:105-115, 1988). Moreover, ErbB2 expression under its endogenous promoter formed DCIS-like mammary tumors in transgenic mice (Andrechek, et al, *Cancer Res.,* 63:4920-4926, 2003).

In response to EGF stimulation, EGFR becomes internalized into clathrin-coated endocytic vesicles and endosomally routed into the multivesicular body (MVB) pathway for sorting to lysosomes for degradation (Baulida, et al., *The Journal of biological chemistry,* 271:5251-5257, 1996; Lenferink, et al., *The EMBO journal,* 17:3385-3397, 1998). Recent studies suggest that EGFR translocates to the nucleus to regulate transcription (Lin et al., 2001). However, ErbB2 is impaired in endocytosis, and ErbB2 dimers are largely recycled back to the plasma membrane for reactivation (Baulida, et al., *The Journal of biological chemistry,* 271: 5251-5257, 1996; Lenferink, et al., *The EMBO journal,* 17:3385-3397, 1998; Sorkin, et al., *Exp. Cell Res.,* 314: 3093-3106, 2008; Waterman, et al., *The Journal of biological chemistry,* 273:13819-13827, 1998). ErbB2 endocytosis impairment involves the chaperon protein HSP90. Inhibition of or dissociation from HSP90 increases ErbB2's interaction with HSP70 and E3 ligase CHIP, and consequently, ErbB2 becomes ubiquitinated and degraded (Austin, et al., *Mol. Biol. Cell,* 15:5268-5282, 2004; Xu, et al., *Proceedings of the National Academy of Sciences of the United States of America,* 99:12847-12852, 2002; Zhou, et al., *The Journal of biological chemistry,* 278:13829-13837, 2003). Moreover, trastuzumab binding to the extracellular domain render ErbB2 degradation through intracellular E3 ligase c-cbl-mediated ubiquitination (Austin, et al., *Mol Biol Cell,* 15:5268-5282, 2004; Klapper, et al., *Cancer Res,* 60:3384-3388, 2000). Exactly how ErbB2 stability is regulated is not well understood. The C-terminus of ErbB2 contains a motif that interacts with the PSD95-Dlg1-zo-1 (PDZ). Interestingly, deletion of critical amino acid residues in this motif accelerates degradation of surface ErbB2 (Shelly, et al., *Developmental cell*, 5:475-486, 2003).

A. Erbin

Erbin is an intracellular protein that was identified by its interaction with ErbB2. It belongs to a unique family of proteins that contain multiple leucine-rich repeats (LRRs) at the N-terminus and a PDZ domain at the C-terminus. Other members of this family include Densin-180 in mammals (Apperson, M. L., et al. *Journal of Neuroscience* 16:6839-6852, 1996), Scribble in *drosophila* (Bilder, et al. *Nature* 2000, 403:676-680, 2000), and LET-413 in *Caenorhabditis elegans* (Legouis, et al. *Nature cell biology*, 2:415-422, 2000). Erbin interacts specifically with ErbB2, but not ErbB3 or ErbB4, via the PDZ domain (Borg, et al., *Nature cell biology*, 2:407-414, 2000; Huang, et al., *The Journal of biological chemistry*, 276:19318-19326, 2001). The interaction can localize ErbB2 to the basolateral membrane of epithelial cells, and thus regulate ErbB2 signaling in epithelia (Borg, et al., *Nature cell biology*, 2:407-414, 2000). Increases and decreases in Erbin levels promote and reduce, respectively, the stability of ErbB2 (Huang, et al., *The Journal of biological chemistry*, 276:19318-19326, 2001; Tao, et al., *Proceedings of the National Academy of Sciences of the United States of America*, 106:9477-9482, 2009). Previous in vitro studies indicated that Erbin was a tumor suppressor. It binds and thus sequesters Smad2/3 in cytosol to inhibit TGF-β signaling activation (Dai, et al., *Molecular and cellular biology* 27:6183-6194, 2007). Erbin overexpression inhibits activation of Erk, probably by disrupting the Sur-8-Ras-Raf complex (Huang, et al., *The Journal of biological chemistry* 278:1108-1114, 2003; Dai, et al., *The Journal of biological chemistry*, 281:927-933, 2006). However, Erbin is redistributed into cytosolic aggregates in basal cell carcinoma together with ErbB2 (Lebeau, et al., *Br. J. Dermatol.*, 152:1248-1255, 2005) and upregulated in colon cancer cells and glioblastoma cells (Dardousis, et al., *Mol Ther* 15:94-102, 2007). Knock-down of Erbin in HT-29 colon cancer cells inhibits its formation of in vitro tumors (Dardousis, et al., *Mol Ther*, 15:94-102, 2007), implying a pro-cancer role of Erbin in epithelial cancer development.

PDZ Domain

The PDZ domain is a common structural domain of approximately 80-90 amino acids found in the signaling proteins of bacteria, yeast, plants, viruses and animals (Boxus, et al., *Retrovirology*, 5:76, 2008; Ponting, *Protein Sci.* 6 (2): 464-468, 1997). PDZ involves the post synaptic density protein (PSD95), *Drosophila* disc large tumor suppressor (Dlg1), and zonula occludens-1 protein (zo-1). Other names for PDZ domains are DHR (Dlg homologous region) or GLGF (glycine-leucine-glycine-phenylalanine) domains (Ponting C P, et al, *Trends Biochem. Sci.*, 20 (3): 102-103, 1995; Cho K O et al. *Neuron*, 9 (5): 929-42, 1992). These domains help anchor transmembrane proteins to the cytoskeleton and hold together signaling complexes (Ranganathan, et al., *Curr. Biol.*, 7 (12): R770-R773, 1997). PDZ domains bind to a region of the C-terminus of other specific proteins, usually by beta sheet augmentation.

The Erbin PDZ domain starts at amino acid 1318 of Erbin (Accession number Q96RT1.2). The amino acid sequence of the PDZ domain is AKQEIRVRVEKDPELGFSISGGVG-GRGNPFRPDDDGIFVTRVQPEGPASK LLQPGDKI-IQANGYSFINIEHGQAVSLLKTFQNTVELIIVREV (SEQ ID NO: 3). Peptides containing the entire PDZ domain or fragments of the PDZ domain can be used to disrupt binding of Erbin to ErbB2. The Erbin peptides can include other amino acids from full length Erbin or can be linked to a targeting peptide or cell-penetrating peptide.

B. Peptide Variants and Derivatives

The disclosed peptides can be modified. As an example, a "methylated derivative" of a peptide refers to a form of the peptide that is methylated. Unless the context indicates otherwise, reference to a methylated derivative of a peptide does not include any modification to the base peptide other than methylation. Methylated derivatives can also have other modifications, but such modifications generally will be noted. For example, conservative variants of an amino acid sequence would include conservative amino acid substitutions of the based amino acid sequence. Thus, reference to, for example, a "methylated derivative" of a specific amino acid sequence "and conservative variants thereof" would include methylated forms of the specific amino acid sequence and methylated forms of the conservative variants of the specific amino acid sequence, but not any other modifications of derivations.

Variants and derivatives are well understood by those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure.

As used herein in reference to a specified amino acid sequence, a "conservative variant" is a sequence in which a first amino acid is replaced by another amino acid or amino acid analog having at least one biochemical property similar to that of the first amino acid; similar properties include, for example, similar size, charge, hydrophobicity or hydrogen-bonding capacity. Conservative variants are also referred to herein as "conservative amino acid substitutions," "conservative amino acid variants," "conservative substitutions," and similar phrase. A "conservative derivative" of a reference sequence refers to an amino acid sequence that differs from the reference sequences only in conservative substitutions.

As an example, a conservative variant can be a sequence in which a first uncharged polar amino acid is conservatively substituted with a second (non-identical) uncharged polar amino acid such as cysteine, serine, threonine, tyrosine, glycine, glutamine or asparagine or an analog thereof. A conservative variant also can be a sequence in which a first basic amino acid is conservatively substituted with a second basic amino acid such as arginine, lysine, histidine, 5-hydroxylysine, N-methyllysine or an analog thereof. Similarly, a conservative variant can be a sequence in which a first hydrophobic amino acid is conservatively substituted with a second hydrophobic amino acid such as alanine, valine, leucine, isoleucine, proline, methionine, phenylalanine or tryptophan or an analog thereof. In the same way, a conservative variant can be a sequence in which a first acidic amino acid is conservatively substituted with a second acidic amino acid such as aspartic acid or glutamic acid or an analog thereof; a sequence in which an aromatic amino acid such as phenylalanine is conservatively substituted with a second aromatic amino acid or amino acid analog, for example, tyrosine; or a sequence in which a first relatively small amino acid such as alanine is substituted with a second relatively small amino acid or amino acid analog such as glycine or valine or an analog thereof. For example, the replacement of one amino acid residue with another that is biologically and/or chemically similar is known to those skilled in the art as a conservative substitution. For example, a conservative substitution would be replacing one hydrophobic residue for another or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein. It is understood that conservative variants of the disclosed amino acid sequences can encompass sequences containing, for example, one, two, three, four or more amino acid substitutions relative to the reference sequence, and that such variants can include naturally and non-naturally occurring amino acid analogs.

Substitutional variants are those in which at least one residue has been removed and a different residue inserted in its place. Examples of such substitutions, referred to as conservative substitutions, can generally be made in accordance with the following Table 1.

TABLE 1

Amino Acid Substitutions
Original Residue Exemplary Conservative
Substitutions, others are known in the art.

| Ala | Ser |
|---|---|
| Arg | Lys; Gln |
| Asn | Gln; His |
| Asp | Glu |
| Cys | Ser |
| Gln | Asn, Lys |
| Glu | Asp |
| Gly | Pro |
| His | Asn;Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity can be made by selecting substitutions that are less conservative, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation. These can be referred to as less conservative variants.

Peptides can have a variety of modifications. Modifications can be used to change or improve the properties of the peptides. For example, the disclosed peptides can be N-methylated, O-methylated, S-methylated, C-methylated, or a combination at one or more amino acids.

The amino and/or carboxy termini of the disclosed peptides can be modified. Amino terminus modifications include methylation (e.g., —NHCH$_3$ or —N(CH$_3$)$_2$), acetylation (e.g., with acetic acid or a halogenated derivative thereof such as α-chloroacetic acid, α-bromoacetic acid, or <-iodoacetic acid), adding a benzyloxycarbonyl (Cbz) group, or blocking the amino terminus with any blocking group containing a carboxylate functionality defined by RCOO— or sulfonyl functionality defined by R—SO$_2$—, where R is selected from the group consisting of alkyl, aryl, heteroaryl, alkyl aryl, and the like, and similar groups. One can also incorporate a desamino acid at the N-terminus (so that there is no N-terminal amino group) to decrease susceptibility to proteases or to restrict the conformation of the peptide compound. In preferred embodiments, the N-terminus is acetylated with acetic acid or acetic anhydride.

Carboxy terminus modifications include replacing the free acid with a carboxamide group or forming a cyclic lactam at the carboxy terminus to introduce structural constraints. One can also cyclize the disclosed peptides, or incorporate a desamino or descarboxy residue at the termini of the peptide, so that there is no terminal amino or carboxyl group, to decrease susceptibility to proteases or to restrict the conformation of the peptide. C-terminal functional groups of the disclosed peptides include amide, amide lower alkyl, amide di(lower alkyl), lower alkoxy, hydroxy, and carboxy, and the lower ester derivatives thereof, and the pharmaceutically acceptable salts thereof.

One can replace the naturally occurring side chains of the genetically encoded amino acids (or the stereoisomeric D amino acids) with other side chains, for instance with groups such as alkyl, lower (C$_{1-6}$) alkyl, cyclic 4-, 5-, 6-, to 7-membered alkyl, amide, amide lower alkyl amide di(lower alkyl), lower alkoxy, hydroxy, carboxy and the lower ester derivatives thereof, and with 4-, 5-, 6-, to 7-membered heterocyclic. In particular, proline analogues in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulfur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g., 1-piperazinyl), piperidyl (e.g., 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g., 1-pyrrolidinyl), pyrrolinyl, pyrrolyl, thiadiazolyl, thiazolyl, thienyl, thiomorpholinyl (e.g., thiomorpholino), and triazolyl. These heterocyclic groups can be substituted or unsubstituted. Where a group is substituted, the substituent can be alkyl, alkoxy, halogen, oxygen, or substituted or unsubstituted phenyl.

Peptides can also be modified by PEGylated. A peptide containing poly(ethylene glycol), PEG, repeat units is also referred to as a "PEGylated" peptide. PEG coupled to peptides can be used for altering solubility characteristics in aqueous or organic solvents for modulation of the immune response to increase the stability of peptides in solution, to enhance the half-life of substances in vivo, to aid in penetrating cell membranes, to alter pharmacological properties to increase biocompatibility, especially toward implanted foreign substances, and to prevent peptide adsorption to surfaces.

The polymer backbone of PEG is not of biological origin and therefore is not readily degraded by mammalian enzymes. This allows for slow degradation of the polymer when used in vivo which extends the half-life of the PEGylated peptide. PEG can be conjugated to other molecules, such as peptides through its two hydroxyl groups at the ends of each linear chain. In some instances this process is done by the creation of a reactive electrophilic intermediate that is capable of spontaneously coupling to nucleophilic residues on a second molecule. Those of skill in the art will know methods and techniques for PEGylating peptides.

One can also readily modify peptides by phosphorylation, and other methods known in the art.

The disclosed peptides also serve as structural models for non-peptidic compounds with similar biological activity. Those of skill in the art recognize that a variety of techniques are available for constructing compounds with the same or similar desired biological activity as the lead peptide compound, but with more favorable activity than the lead with respect to solubility, stability, and susceptibility to hydrolysis and proteolysis (See, Morgan and Gainor, *Ann. Rep. Med. Chem.*, 24:243-252, 1989). These techniques include, but are not limited to, replacing the peptide backbone with a backbone composed of phosphonates, amidates, carbamates, sulfonamides, secondary amines, and N-methylamino acids.

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—$CH$=$CH$— (cis and trans), —$COCH_2$—$CH(OH)CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, *Trends Pharm. Sci.*, (1980) pp. 463-468; Hudson, D. et al., *Int. J. Pept. Prot. Res.*, 14:177-185 (1979) (—$CH_2NH$—, $CH_2CH_2$); Spatola et al., *Life Sci.*, 38:1243-1249 (1986) (—$CHH_2$—S); Hann, *J. Chem. Soc. Perkin Trans.*, I 307-314 (1982) (—$CH$—$CH$—, cis and trans); Almquist et al., *J. Med. Chem.*, 23:1392-1398 (1980) (—$COCH_2$—); Jennings-White et al., *Tetrahedron Lett.*, 23:2533 (1982) (—$COCH_2$—); Szelke et al., European Appln, EP 45665 CA (1982): 97:39405 (1982) (—$CH(OH)CH_2$—); Holladay et al., *Tetrahedron Lett.*, 24:4401-4404 (1983) (—$C(OH)CH_2$—); and Hruby, *Life Sci.*, 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as β-alanine, γ-aminobutyric acid, and the like.

Substitutional or deletional mutagenesis can be employed to insert sites for N-glycosylation (Asn-X-Thr/Ser) or O-glycosylation (Ser or Thr). Deletions of cysteine or other labile residues also can be desirable. Deletions or substitutions of potential proteolysis sites, e.g. Arg, can be accomplished, for example, by deleting one of the basic residues or substituting one by glutaminyl or histidyl residues.

Certain post-translational derivatizations can be the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T.E. Creighton, Proteins: Structure and Molecular Properties, W. H. Freeman & Co., San Francisco, pp 79-86 [1983]), acetylation of the N-terminal amine and, in some instances, amidation of the C-terminal carboxyl.

1. Homology

One way to define the variants and derivatives of the disclosed amino acids sequences, amino acid segments, peptides, proteins, etc. herein is through defining the variants and derivatives in terms of homology/identity to specific known sequences. For example, specifically disclosed are variants of these and other amino acids sequences, amino acid segments, peptides, proteins, etc. herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, *J. MoL Biol.*, 48: 443 (1970), by the search for similarity method of Pearson and Lipman, *Proc. Natl. Acad. Sci. U.S.A.*, 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, *Science,* 244:48-52, 1989, Jaeger, et al., *Proc. Natl. Acad. Sci. USA,* 86:7706-7710, 1989, Jaeger, et al., *Methods Enzymol.,* 183:281-306, 1989 which are herein incorporated by reference for at least material related to nucleic acid alignment.

It is understood that the description of conservative variants and homology can be combined together in any combination, such as embodiments that have at least 70% homology to a particular sequence wherein the variants are conservative variants.

2. Peptidomimetic

A peptidomimetic can be substituted for any of the disclosed peptides. For example, a multivalent peptide can contain at least one peptidomimetic fused to either a peptide or to another peptidomimetic. A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; α,α.-dialkylglycine or α-aminocycloalkane carboxylic acid; an N$^α$-C$^α$ cyclized amino acid; an N$^α$.-methylated amino acid; a β- or -amino cycloalkane carboxylic acid; an a β-unsaturated amino acid; a β,β-dimethyl or β-methyl amino acid; a β-substituted-2,3-methano amino acid; a cyclized amino acid; L-(-amino butyric acid, L-(-amino isobutyric acid, 7-amino heptanoic acid, L-aspartic acid, L-glutamic acid, L-methionine sulfone, L-norleucine, L-norvaline, Boc-p-nitro-L-phenylalanine, Boc-hydroxyproline, and Boc-L-thioprolinea, substituted proline or another amino acid mimetic. A peptidomimetic which mimics peptide secondary structure can contain, for example, a non-peptidic β-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylene-sulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Methods for identifying a peptidomimetic are well known in the art and include, for example, the screening of databases that contain libraries of potential peptidomimetics.

There are also numerous D amino acids or amino acids which have a different functional substituent than natural amino acids. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., *Methods in Molec. Biol.*, 77:43-73 (1991), Zoller, *Current Opinion in Biotechnology*, 3:348-354 (1992); Ibba, *Biotechnology & Genetic Engineering Reviews*, 13:197-216 (1995), Cahill et al., *TIBS*, 14(10):400-403 (1989); Benner, *TIB Tech*, 12:158-163 (1994); Ibba, et al., *Bio/technology*, 12:678-682 (1994) all of which are herein incorporated by reference at least for material related to amino acid analogs). D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides.

2. Nucleic Acids Encoding the Peptides

Nucleic acids that can encode the disclosed peptides are readily ascertainably by one of skilled in the art. Thus, disclosed are all nucleic acids, including degenerate nucleic acids, encoding the disclosed peptide sequences. While each particular nucleic acid sequence may not be written out, it is understood that each and every sequence is in fact disclosed and described through the disclosed peptide sequences.

3. Protein Transduction Domain

The disclosed peptides can be modified to include a protein transduction domain (PTD). As used herein, a "protein transduction domain" or PTD refers to a polypeptide, polynucleotide, carbohydrate, organic or inorganic compound that facilitates traversing a lipid bilayer, micelle, cell membrane, organelle membrane, or vesicle membrane. A PTD attached to another molecule facilitates the molecule traversing membranes, for example going from extracellular space to intracellular space, or cytosol to within an organelle.

In some embodiments, the protein transduction domain is a polypeptide. A protein transduction domain can be a polypeptide including positively charged amino acids. Thus, some embodiments include PTDs that are cationic or amphipathic. Protein transduction domains (PTD), also known as a cell penetrating peptides (CPP), are typically polypeptides including positively charged amino acids. PTDs are known in the art, and include but are not limited to small regions of proteins that are able to cross a cell membrane in a receptor-independent mechanism (Kabouridis, *Trends in Biotechnology*, (11):498-503 (2003)). Although several PTDs have been documented, the two most commonly employed PTDs are derived from TAT (Franke, et al., *Cell*, 55(6):1189-93(1988)) protein of HIV and Antennapedia transcription factor from *Drosophila*, whose PTD is known as Penetratin (Derossi, et al., *J. Biol. Chem.*, 269(14):10444-50 (1994)). Exemplary protein transduction domains include polypeptides with 11 Arginine residues, or positively charged polypeptides or polynucleotides having 8-15 residues, preferably 9-11 residues.

The Antennapedia homeodomain is 68 amino acid residues long and contains four alpha helices. Penetratin is an active domain of this protein which consists of a 16 amino acid sequence derived from the third helix of Antennapedia. TAT protein consists of 86 amino acids and is involved in the replication of HIV-1. The TAT PTD consists of an 11 amino acid sequence domain (residues 47 to 57; YGRKKRRQRRR (SEQ ID NO: [[3]] 4) (SEQ ID NO: [[3]] 4) of the parent protein that appears to be critical for uptake. Additionally, the basic domain Tat (49-57) or RKKRRQRRR (SEQ ID NO:[[4]] 5) has been shown to be a PTD. In the current literature TAT has been favored for fusion to proteins of interest for cellular import. Several modifications to TAT, including substitutions of Glutatmine to Alanine, i.e., Q A, have demonstrated an increase in cellular uptake anywhere from 90% (Wender, et al., *Proc. Natl. Acad. Sci. USA.*, 97(24):13003-8 (2000)) to up to 33 fold in mammalian cells. (Ho, et al., *Cancer Res.*, 61(2):474-7 (2001)).

PTDs can include a sequence of multiple arginine residues, referred to herein as poly-arginine or poly-ARG. In some embodiments the sequence of arginine residues is consecutive. In some embodiments the sequence of arginine residues is non-consecutive. A poly-ARG can include at least 7 arginine residues, more preferably at least 8 arginine residues, most preferably at least 11 arginine residues. In some embodiments, the poly-ARG includes between 7 and 15 arginine residues, more preferably between 8 and 15 arginine residues. In some embodiments the poly-ARG includes between 7 and 15, more preferably between 8 and 15 consecutive arginine residues. An example of a poly-ARG is RRRRRRR (SEQ ID NO:[[5]] 6). Additional exemplary PTDs include but are not limited to; RRQRRTSKLM KR (SEQ ID NO:[[6]] 7); GWTLNSAGYL LGKINLKALA ALAKKIL (SEQ ID NO:[[7]] 8); WEAKLAKALA KALAKHLAKA LAKALKCEA (SEQ ID NO:[[8]] 9); and RQIKIWFQNR RMKWKK (SEQ ID NO:[[9]] 10).

Without being bound by theory, it is believed that following an initial ionic cell-surface interaction, some polypeptides containing a protein transduction domain are rapidly internalized by cells via lipid raft-dependent macropinocytosis. For example, transduction of a TAT-fusion protein was found to be independent of interleukin-2 receptor/raft-, caveolar- and clathrin-mediated endocytosis and phagocytosis (Wadia, et al., *Nature Medicine,* 10:310-315 (2004), and Barka, et al., *J. Histochem. Cytochem.,* 48(11):1453-60 (2000)). Therefore, in some embodiments the disclosed compositions include an endosomal escape sequence that enhances escape of the compositions from macropinosomes. In some embodiments the endosomal escape sequence is part of, or consecutive with, the protein transduction domain. In some embodiments, the endosomal escape sequence is non-consecutive with the protein transduction domain. In some embodiments the endosomal escape sequence includes a portion of the hemagglutinin peptide from influenza (HA). One example of an endosomal escape sequence includes GDIMGEWG NEIFGAIAGF LG (SEQ ID NO: 11). In one embodiment a protein transduction domain including an endosomal escape sequence includes the amino acid sequence RRRRRRRRRR RGEGDIMGEW GNEIFGAIAG FLGGE (SEQ ID NO: 12).

In some embodiments the protein transduction domain or endosomal escape sequence can be cleaved from the protein specific peptide.

III. Methods of Using ErB2 Peptides

A. Disrupting the Erbin-ErbB2 Interaction

Regulation of ErbB2 by Erbin requires interaction between the two proteins. Erbin interacts directly with ErbB2 to prevent it from being degraded; it also promotes the dimerization of the kinase to increase its activity. Although ErbB2 overexpression is due to gene amplication, a posttranslational mechanism can be used to regulate the function of ErbB2. In particular, this mechanism can involve disrupting the Erbin-ErbB2 interaction ErbB2 and Erbin peptides can both, alone or in combination, be used to disrupt the Erbin-ErbB2 interaction. As an example, the ErbB2 peptide, PTAENPEYLGLDVPV (SEQ ID NO:1), can be used. In some instances, the ErbB2 peptide is linked to a PTD, such as Tat, resulting in the peptide YGRKKRRQRRR-G-PTAENPEYLGLDVPV (SEQ ID NO:2). YGRKKRRQRRR (SEQ ID NO: 13) is the Tat sequence, -G- is a linker amino acid, and PTAENPEYL-GLDVPV (SEQ ID NO:1) is the ErbB2 fragment. The PTD can be linked to the N-terminal or C-terminal end of the peptide.

In addition to Erbin PDZ and B2tail, the Erbin-ErbB2 interaction can be disrupted by other means including, but not limited to, small molecules, antibodies, and peptide derivatives.

B. Treating ErbB2-Dependent Cancer

Methods of treating ErbB2-dependent cancer include the administration of a composition that inhibits the interaction of Erbin and ErbB2. Preventing Erbin's regulation of ErbB2 leads to an increase of ErbB2 degradation, reduction of ErbB2 activity, and inhibition of the growth of tumor cells. ErbB2 levels are important in breast cancer development and progression. ErbB2 expression correlates with high recurrence, malignant metastasis, and poor prognosis of breast cancers. The ErbB2-Erbin interaction is involved in tumorigenesis and tumor metastasis. Erbin is required for ErbB2-dependent growth or proliferation of breast cancer cells. Erbin's role involves increasing ErbB2 stability. Therefore, without Erbin or without the Erbin-ErbB2 interaction, ErbB2 function is impaired and its tumorigenesis and metastasis properties are reduced.

Administration of ErbB2 or Erbin peptides can inhibit the Erbin-ErbB2 interaction and prevent ErbB2 from causing tumor growth and metastasis. In one instance, the ErbB2 peptide is a C-terminal fragment that interacts with the PDZ domain of Erbin. The peptide can contain the amino acid sequence PTAENPEYLGLDVPV (SEQ ID NO:1)

ErbB2-dependent cancers include, but are not limited to, cancers in the mammary glands, ovaries, stomach, and uterus.

C. Combination Therapy

A combination therapy can be used to treat ErbB2-dependent cancers. An ErbB2 or Erbin peptide can be used in combination with a an ErbB2 peptide, Erbin peptide, ErbB2 or Erbin antibody, ErbB kinase inhibitors, any other composition that disrupts the interaction of ErbB2 and Erbin, or any other composition that is used to treat an ErbB2-dependent cancer. The therapeutics can have similar or distinct mechanisms. For example, an ErbB2 peptide can be used in combination with a chemotherapeutic agent. The ErbB2 peptide can be YGRKKRRQRRR-G-PTAENPEYL-GLDVPV (SEQ ID NO:2).

Combination therapies can be used as the initial treatment or can be used for treating cancers that are resistant to a single treatment. In some instances combination therapies are more effective than single therapeutic treatments.

Two or more compositions can be used together or sequentially. They can be formulated together or separately.

IV. Methods of Administration

In general, methods of administering compositions, including peptides, are well known in the art. In particular, the routes of administration already in use for peptide therapeutics, along with formulations in current use, provide preferred routes of administration and formulation for the peptides described above.

Compositions can be administered by a number of routes including, but not limited to: oral, intravenous, intraperitoneal, intramuscular, transdermal, subcutaneous, topical, sublingual, or rectal means. Compositions can also be administered via liposomes. Such administration routes and appropriate formulations are generally known to those of skill in the art.

Administration of the formulations described herein may be accomplished by any acceptable method which allows the compositions, for example the peptide or nucleic acid encoding the peptide, to reach its target. The particular mode selected will depend of course, upon factors such as the particular formulation, the severity of the state of the subject being treated, and the dosage required for therapeutic efficacy. As generally used herein, an "effective amount" is that amount which is able to treat one or more symptoms of ErbB2-dependent disorders, reverse the progression of one or more symptoms, halt the progression of one or more symptoms, or prevent the occurrence of one or more symptoms of ErbB2-dependent disorders in a subject to whom the formulation is administered, as compared to a matched subject not receiving the composition. The actual effective amounts of the composition can vary according to the specific composition or combination thereof being utilized, the particular composition formulated, the mode of administration, and the age, weight, condition of the individual, and severity of the symptoms or condition being treated.

Any acceptable method known to one of ordinary skill in the art may be used to administer a formulation to the subject. The administration may be localized (i.e., to a particular region, physiological system, tissue, organ, or cell type) or systemic, depending on the condition being treated.

Injections can be e.g., intravenous, intradermal, subcutaneous, intramuscular, or intraperitoneal. In some embodiments, the injections can be given at multiple locations. Implantation includes inserting implantable drug delivery systems, e.g., microspheres, hydrogels, polymeric reservoirs, cholesterol matrixes, polymeric systems, e.g., matrix erosion and/or diffusion systems and non-polymeric systems, e.g., compressed, fused, or partially-fused pellets. Inhalation includes administering the composition with an aerosol in an inhaler, either alone or attached to a carrier that can be absorbed. For systemic administration, it may be preferred that the composition is encapsulated in liposomes.

The nucleic acid may be delivered in a manner which enables tissue-specific uptake of the agent and/or nucleic acid delivery system.

The formulations may be delivered using a bioerodible implant by way of diffusion or by degradation of the polymeric matrix. In certain embodiments, the administration of the formulation may be designed so as to result in sequential exposures to the peptide over a certain time period, for example, hours, days, weeks, months or years. This may be accomplished, for example, by repeated administrations of a formulation or by a sustained or controlled release delivery system in which the composition is delivered over a prolonged period without repeated administrations. Administration of the formulations using such a delivery system may be, for example, by oral dosage forms, bolus injections, transdermal patches or subcutaneous implants. Maintaining a substantially constant concentration of the composition may be preferred in some cases.

Other delivery systems suitable include time-release, delayed release, sustained release, or controlled release delivery systems. Such systems may avoid repeated administrations in many cases, increasing convenience to the subject and the physician. Many types of release delivery systems are available and known to those of ordinary skill in the art. They include, for example, polymer-based systems such as polylactic and/or polyglycolic acids, polyanhydrides, polycaprolactones, copolyoxalates, polyesteramides, polyorthoesters, polyhydroxybutyric acid, and/or combinations of these. Microcapsules of the foregoing polymers containing nucleic acids are described in, for example, U.S. Pat. No. 5,075,109. Other examples include nonpolymer systems that are lipid-based including sterols such as cholesterol, cholesterol esters, and fatty acids or neutral fats such as mono-, di- and triglycerides; hydrogel release systems; liposome-based systems; phospholipid based-systems; silastic systems; peptide based systems; wax coatings; compressed tablets using conventional binders and excipients; or partially fused implants. Specific examples include erosional systems in which the peptide is contained in a formulation within a matrix (for example, as described in U.S. Pat. Nos. 4,452,775, 4,675,189, 5,736,152, 4,667,013, 4,748,034 and 5,239,660), or diffusional systems in which an active component controls the release rate (for example, as described in U.S. Pat. Nos. 3,832,253, 3,854,480, 5,133,974 and 5,407,686). The formulation may be as, for example, microspheres, hydrogels, polymeric reservoirs, cholesterol matrices, or polymeric systems. In some embodiments, the system may allow sustained or controlled release of the composition to occur, for example, through control of the diffusion or erosion/degradation rate of the formulation containing the peptide. In addition, a pump-based hardware delivery system may be used to deliver one or more embodiments.

Examples of systems in which release occurs in bursts includes, e.g., systems in which the composition is entrapped in liposomes which are encapsulated in a polymer matrix, the liposomes being sensitive to specific stimuli, e.g., temperature, pH, light or a degrading enzyme and systems in which the composition is encapsulated by an ionically-coated microcapsule with a microcapsule core degrading enzyme. Examples of systems in which release of the inhibitor is gradual and continuous include, e.g., erosional systems in which the composition is contained in a form within a matrix and effusional systems in which the composition permeates at a controlled rate, e.g., through a polymer. Such sustained release systems can be e.g., in the form of pellets, or capsules.

Use of a long-term release implant may be particularly suitable in some embodiments. "Long-term release," as used herein, means that the implant containing the composition is constructed and arranged to deliver therapeutically effective levels of the composition for at least 30 or 45 days, and preferably at least 60 or 90 days, or even longer in some cases. Long-term release implants are well known to those of ordinary skill in the art, and include some of the release systems described above.

Effective Dosages

Dosages for a particular individual can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to an individual is sufficient to effect a beneficial therapeutic response in the individual over time, or, e.g., to reduce symptoms, or other appropriate activity, depending on the application. The dose is determined by the efficacy of the particular formulation, and the activity, stability or serum half-life of the peptide employed and the condition of the individual, as well as the body weight or surface area of the individual to be treated. The size of the dose is also determined by the existence, nature, and extent of any adverse side-effects that accompany the administration of a particular vector, formulation, or the like in a particular individual.

EXAMPLES

Materials and Methods

Animals

MMTV-neu (Stock. 002376) and MMTV-PyVT mice (Stock. 002374) were from Jackson Laboratory. Both erbin$^{-/-}$ and erbin$^{\Delta C/\Delta C}$ mice were described previously [[57]]. Exons 1 and 2 were replaced by a neomycin-resistant marker in erbin$^{-/-}$ mice. In erbin$^{\Delta C/\Delta C}$ mice, the lacZ gene was inserted downstream of exon 20 of the erbin gene, whereby the mutant mice express a fusion protein containing the N-terminal 693 aa residues of Erbin and β-galactosidase (thus named as Erbin$_{1-693}$β-gal). Mice were backcrossed into FVB background and littermates or sisters were kept as virgin for experiments. Mice were housed in a room with a 12-h light/dark cycle with access to food and water ad libitum. Animal experiments were approved by the Institutional Animal Care and Use Committee of the Georgia Health Sciences University, and the French Guidelines for Animal Handling.

Constructs, Antibodies and Reagents pFlag-CMV1-ErbB2, pcDNA3-ErbB3, pRK5-Myc-Erbin, pRK5-Myc-Erbin-LRR, pRK5-Myc-Erbin-ΔLAP-APDZ, pRK5-Myc-Erbin965, and pKH3-HA-Erbin constructs were described previously (Tao, Y., et al PNAS 106, 9477-9482, 2009). pMyc-CMV1-ErbB2 was made by inserting Myc tag to replace Flag in pFlag-CMV1-ErbB. PLL3.7, pLP1, pLP2, VSVG plasmids were kindly provided by Dr. Quansheng Du. shErbin was generated by subcloning the oligonucleotide DNA between HpaI and XhoI in PLL3.7: forward: 5'TGCAT CCCTC TAGAG AACAA CTTTC AAGAG AAGTT GTTCT CTAGA GGGAT GCTTT TTTC (SEQ ID NO:14); reverse: 5'TCGAG AAAAA AGCAT CCCTC TAGAG AACAA CTTCT CTTGA AAGTT GTTCT CTAGA GGGAT GCA (SEQ ID NO:15). All plasmids were verified by sequencing. TAT-B2tail peptide containing the TAT sequence and ErbB2 last 15 amino acids (YGRKKRRQRRR-G-PTAENPEYLGLD-VPV (SEQ ID NO:2) was synthesized by NeoBioSci Company.

Erbin antibody was generated by immunizing rabbits with GST-Erbin (aa 465-818) as described previously[[47]]. It was purified by GST-Erbin immobilized on Affi-Gel 10, following the manufacturer's instruction. Information on commercial rabbit polyclonal antibodies is as follows: ErbB2 (sc-284, Santa Cruz), ErbB3 (sc-285, Santa Cruz), ErbB4 (sc-283, Santa Cruz), EGFR (sc-374607, Santa Cruz), NRG1 (sc-348, Santa Cruz), K14 (sc-53253, Santa Cruz), K8/K18 (sc-52325, Santa Cruz), pErbB2 (2243, Cell Signaling), δ-catenin (C98320, BD Transduction Laboratories). Information on commercial mouse antibodies is as follows: α-tubulin (sc-8035, Santa Cruz), β-actin (sc-130300, Santa Cruz), GAPDH (MAB374, Millipore), 4G10 (16-105, Upstate), Ki67 (9106-S, Thermo). Alexa Fluor® 488- and Alexa Fluor® 594-conjugated secondary antibodies were purchased from Molecular Probes, and HRP-conjugated antibodies were from Amersham Biosciences. Cycloheximide was from Calbiochem; MG132 was from BostonBiochem. All other chemicals were from Sigma-Aldrich.

Human Breast Tissue Specimens

Human primary breast specimens of paraffin-embedded tissue blocks were obtained from the Department of Pathology and a tissue bank at the Center for Experimental Medicine, the First Affiliated Hospital, Nanchang University, China. Specimens were collected and processed in compliance with protocols approved by the Institutional Review Board. Detailed clinical and pathological information of the patients is summarized in Table 2.

Cell Culture and Transfection

HEK293 cells were transfected using polyethylenimine (PEI) as described (Simeone, L., et al. J Neurosci 30, 6620-6634, 2010). Briefly, cells were cultured in 6-well plates to 80% confluence, and incubated for 6 hour with precipitates formed by 2 µg of plasmid DNA and 2 µl of 0.5% (w/v, pH 7.0) PEI (Sigma-Aldrich, cat. No 40,872-7). After replacing with fresh medium, cells were cultured in DMEM containing 10% FBS for 48 hour before harvesting. MCF10A cells and breast cancer cells were cultured as described previously (Lu, J., et al. Cancer cell 16, 195-207, 2009). Briefly, MCF10A cells were grown in DMEM/F12 supplemented with 2% horse serum, 10 µg/ml insulin, 100 ng/ml cholera toxin, 0.5 µg/ml hydrocortisone, 50 U/ml penicillin and 50 µg/ml streptomycin. ZR751 breast cells were cultured in DMEM/F12 containing 10% FBS. SKBR3 and BT474 breast cells were cultured in RPMI medium containing 10% FBS.

Lentivirus Packaging and Infection

HEK293FT cells (in 10-cm dish) were co-transfected by PEI with PLL3.7 or shErbin with PLP1, PLP2 and VSVG with a ratio of 7.5:2.5:2.5:2.5 (µg), following an established protocol (Tiscornia, G., et al. Nat Protoc 1, 241-245, 2006). Six hours later, cells were changed to DMEM/10% FBS and cultured for additional 24 hours. For infection, cells were incubated for 4 days with virus in the presence of polybrene (5 µg/ml) to increase infection efficiency. Infected cells were sorted by expression of GFP to establish stable lines. In some experiments, virus-infected MCF10A cells were cotransfected with pFlag-CMV1-ErbB2 and pcDNA3.1 (encoding neomycin resistance) (10:1) and screened for stable lines by G418.

Matrigel 3D Culture

Matrigel 3D culture of MCF10A cells was established as described previously (Muthuswamy, et al., Nature cell biology, 3, 785-792, 2001). Briefly, Lab-Tek 8-chamber slides (Thermo) were coated with 35 µl Matrigel (Falcon BD) per well and left to solidify for 15 minutes at 37° C. MCF10A cells were suspended at a concentration of $10^5$ cells per 4.0 ml in DMEM/F12 supplemented with 2% horse serum, 10 µg/ml insulin, 100 ng/ml cholera toxin, 0.5 µg/ml hydrocortisone, 50 U/ml penicillin and 50 µg/ml streptomycin and mixed 1:1 with medium containing 4% Matrigel and 10 ng/ml EGF. Cell mixture (400 µl) were added to each Matrigel-coated chamber. The medium was replaced every 4 days with the assay medium containing 5 ng/ml EGF. Twelve days later, cells were fixed by 4% polyformaldhyde (PFA) for analysis.

MTS Assay

Cell proliferation was measured by MTS assay, as described previously (Zhang, S., et al., Nature medicine, 17, 461-469, 2011). Cells were seeded at a density of 5,000 cells/well in 96-well plate, and incubated with 20 µl MTS [3-(4,5-dimethyl-2-yl)-5-(3-carboxymethoxyphenyl)-2-(4-sulfophenyl)-2H-tetrazolium, inner salt; MTS] at 37° C. for 2 hours. Optical density was measured at wavelength of 490 nm.

Immunofluorescence and Immunohistochemistry

Cells cultured on coverslips were fixed in 4% PFA in PBS and incubated at 4° C. for 30 minutes with 0.3% Triton-X-100. Paraffin- or OCT-embedded mouse tissue sections were cut into 20 µm sections and mounted on SuperFrost plus slides, fixed and subjected to hematoxylin/eosin (H & E) staining and/or immunostaining. For immunostaining, fixed slides and cells were incubated at 4° C. overnight with primary antibodies in PBS containing 0.5% goat serum, 1% BSA and 0.1% Triton-X-100. After washing 3 times with PBS, samples were incubated at room temperature for 1 hour with Alexa-488 or -594 goat anti-rabbit/mouse secondary antibody, and mounted with Vectashield mounting medium (Vector). Images were taken by a Zeiss LSM510 confocal microscope and analyzed by software Image J (NIH).

Immunohistochemical staining was performed as described previously (Pan, X., et al. Nature medicine 17, 708-714, 2011). Paraffin-embedded human specimens were cut into 3 µm sections, mounted on slides. Tissue sections were deparaffinized with xylene, rehydrated through a graded alcohol series, and incubated in 3% hydrogen peroxide to block endogenous peroxidase activity. Sections were incubated in 10 mM sodium citrate buffer (pH 6.0) at sub-boiling temperatures for 10 min, rinsed in PBS, and incubated with 10% normal goat serum to block non-specific staining. Sections were incubated with a primary antibody (1:200) at 4° C. in a humidified chamber overnight and immunoreactivity was visualized by using the Polink-2 HRP DAB Detection kit following the manufacturer's procedure. Images were captured with a FSX100 microscope equipped with a digital camera system (Olympus). Samples were examined by 3 investigators who were blind to pathological information by using the German semi-quantitative scoring method (Zaineddin, A. K., et al., *International journal of cancer*, 130, 1401-1410, 2012; Remmele, et al., *Pathol. Res. Pract.*, 189, 862-866, 1993; Pan, X., et al., *Nature medicine*, 17, 708-714, 2011). Each specimen was scored for intensity of nucleic, cytoplasmic, and membrane staining (no staining=0; weak staining=1, moderate staining=2, strong staining=3) and for extent of stained cells (0%=0, 1~24%=1, 25~49%=2, 50~74%=3, 75~100%=4). Final immunoreactive score was product of intensity score multiplies extent score. Consecutive sections were stained by H & E to help localize cancer tissues and adjacent normal epithelium.

Whole Mount Staining of Mammary Glands

Whole mount hematoxylin staining of mammary glands was performed as described previously, with modification (Webster, M. A., et al. Molecular and cellular biology 18, 2344-2359, 1998). Briefly, mammary fat pads were spread on glass slides, air dried overnight, and fixed in acetone for 12 hours. Samples were stained by Harris modified hematoxylin solution (Sigma-Aldrich, HHS16) for overnight, and destained in 1% HCl in 75% ethanol until epithelial components of the mammary gland were visible. Stained samples were rinsed for 30 sec in 0.002% $NH_4OH$, dehydrated in a series of increasing concentrations of ethanol (50%, 70%, 90% and 100%), and incubated in 100% xylenes overnight. Mammary fat pads were mounted by Permount mounting medium (Fisher) and examined under Zeiss Axiophot microscope.

X-Gal In Situ Assay

Mammary fat pads were mounted on SuperFrost plus slides and fixed for 30 minutes in 2% formalin/1% glutaraldehyde at 4° C. Whole mount samples were incubated at 37° C. with 1 mg/ml X-gal overnight. After washing, samples were counter-stained with nuclear fast red, and covered with coverslips in Immu-Mount (Fisher). For serial sections, isolated mammary fat pads were fixed and stained with X-gal. Tissues were embedded in paraffin and sectioned for observation.

Protein Interaction and Western Blotting

For immunoprecipitation, cells were lysed in lysis buffer (50 mM Tris-HCl, pH 7.4, 150 mM NaCl, 1% NP-40, 0.5% Triton-X-100, 1 mM PMSF, 1 mM EDTA, 5 mM NaF, 2 mM $Na_3VO_4$, and protease inhibitor cocktails). Pre-cleared cell lysates were incubated with 1 µg of indicated antibodies at 4° C. overnight, in the absence or presence of ErbB2 or Erbin peptides to block the ErbB2-Erbin interaction. The reaction was incubated with 50 µl of 1:1 slurry beads conjugated with protein G or A (Roche) for 3 hours. Beads were washed 4 times with lysis buffer before the addition of SDS sample buffer and subjected to Western blot analysis as described previously (Shen, C., et al., *JBC*, 283, 17721-17730, 2008). Immunoreactive bands were visualized using enhanced chemiluminescence (Pierce), scanned with an Epson 1680 scanner, and analyzed with Image J.

Statistical Analyses

Data were analyzed by paired or unpaired t-test or one-way ANOVA. Correlation data of human samples were analyzed by Pearson's correlation test. Difference between groups was assessed by one-way ANOVA. The $\chi^2$ test was used to analyze correlation between Erbin expression and clinicopathologic characteristics. Unless otherwise indicated, data were expressed as mean±SD. Statistical significance was considered when P is smaller than 0.05.

Example 1

Erbin Expression in Luminal Epithelial Cells of Mammary Glands

Figure 2A:
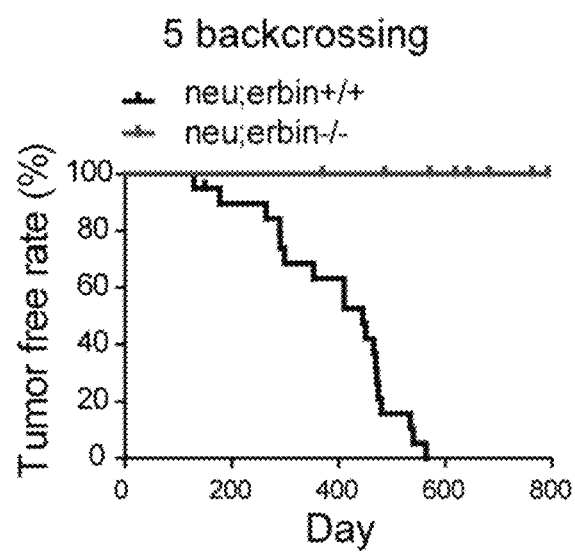
FIGS. 2A-2E show a critical role for Erbin in ErbB2-dependent tumorigenesis in vivo. (A) Erbin mutation inhibited tumorigenesis in MMTV-neu mice on incipient congenic FVB background. erbin$^{+/+}$ and erbin$^{-/-}$ mice were backcrossed for 5 generations with FVB wild types and then crossed with FVB-congenic MMTV-neu. Virgin littermates of MMTV-neu; erbin$^{-/-}$ and MMTV-neu; erbin$^{+/+}$ mice (n=18 and 20, respectively) were examined for tumor by weekly palpation. Kaplan-Meier survival plot. Log-rank (Mantel-Cox) test, P<0.0001. (B)-(C) Erbin mutation delayed ErbB2-dependent tumorigenesis in MMTV-neu mice on congenic FVB background. erbin$^{+/+}$ and erbin$^{-/-}$ mice were backcrossed for 12 generations with FVB wild types and then crossed with FVB-congenic MMTV-neu. Virgin littermates of MMTV-neu; erbin$^{-/-}$ and MMTV-neu; erbin$^{+/+}$ mice (n=22 and 28, respectively) were examined for tumor by weekly palpation. (B) Kaplan-Meier survival plot. Log-rank (Mantel-Cox) test, P<0.0001. (C) Reduced tumor volumes in MMTV-neu; erbin$^{-/-}$, compared to MMTV-neu; erbin$^{+/+}$ littermates. Volumes were measured 5 weeks after first detection of tumors by palpation. (n=10 and 10, respectively. **P<0.01). (D)-(E) Erbin mutation had no effect on tumorigenesis in MMTV-PyVT mice. Virgin littermates of MMTV-PyVT; erbin$^{+/+}$ (n=22) and MMTV-PyVT; erbin$^{-/-}$ (n=16) mice were examined for tumor by weekly palpation. (D) Kaplan-Meier survival plot. Log-rank (Mantel-Cox) test, P>0.05. (E) Erbin depletion had no effect on breast tumor growth in MMTV-PyVT mice. n=8, P=0.128.

In order to assess the role of Erbin in ErbB2 tumorigenicity in vivo, the expression of Erbin was first determined in murine mammary glands. Mammary fat pads were isolated from adult wild type mice (erbin$^{+/+}$) and Erbin null (erbin$^{-/-}$) mice and homogenized. Homogenates were subjected to Western blot analysis using affinity-purified anti-Erbin antibody. A dominant band was identified which migrated at predicated 180 kDa as well as a weak band with smaller molecular weight. Both bands disappeared in samples isolated from erbin$^{-/-}$ mice, indicating that they represent full length Erbin and a likely proteolytic product. These results indicate that Erbin is expressed in mammary glands and is specifically recognized by the anti-Erbin antibody. To determine which cells express Erbin, sections of mammary glands were immunostained with the anti-Erbin antibody. Luminal epithelial cells expressed δ-catenin, a p120-catenin family protein known to be enriched at adherence junctions (Anastasiadis, et al. *J Cell Sci* 113 (Pt 8), 1319-1334, 2000). Interestingly, Erbin immunoreactivity was present almost exclusively in δ-catenin-positive, luminal epithelial cells (FIG. 2A), indicating that Erbin is expressed in luminal epithelial cells of mammary glands. This staining was specific because, first, the signal was abolished in sections isolated from erbin$^{-/-}$ mice (FIG. 2A). Second, it was not detectable in myoepithelial cells that were also labeled by anti-δ-catenin antibody (FIG. 2A). In addition, mammary gland sections were co-stained with antibodies directed against Erbin and cytokeratins K8/K18 and K14, markers of luminal and myoepithelial cells, respectively (data not shown). Erbin colocalized with K8/K18 but not K14. These results show specific expression of Erbin in luminal epithelial cells of mouse mammary glands.

Figure 8:
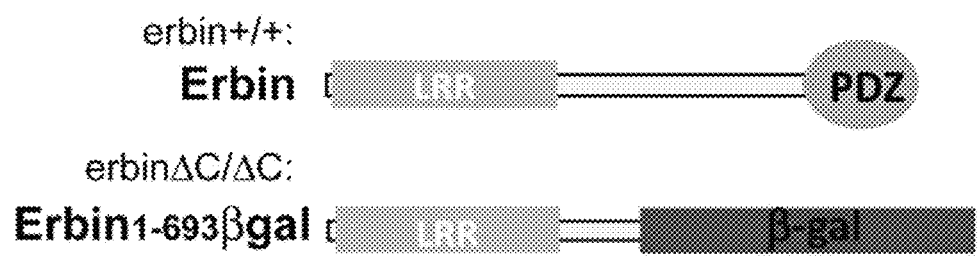
FIG. 8 is a schematic diagram illustrating domain structures of wild type Erbin and Erbin$_{1-693}$-βgal in erbin$^{\Delta C/\Delta C}$ mice. Note that β-gal is expressed as a fusion with truncated Erbin. β-gal activity was detected in mammary epithelial ducts in erbin$^{+/\Delta C}$ mice. Mammary fat pads were isolated from erbin$^{+/\Delta C}$ mice and whole mount stained for β-gal in situ activity. β-gal activity was confined in epithelial cells of mammary ducts. Shown is a representative image of X-gal-stained mammary gland section from erbin$^{+/\Delta C}$ mice. (data not shown).

To further determine where Erbin is expressed in mammary glands, breast fat pads were isolated from erbin$^{+/\Delta C}$ mice and subjected to X-gal staining. In erbin$^{+/\Delta C}$ mice, one allele of the erbin gene is disrupted by a lacZ gene which was inserted in intron 20 (Tao, Y., et al. *PNAS*, 106, 9477-9482, 2009). Thus, erbin$^{+/\Delta C}$ mice express a fusion protein, Erbin$_{1-693}$βgal, which contains the N-terminal region of Erbin (aa 1-693) and β-gal (FIG. 8). Because the expression of Erbin$_{1-693}$βgal remains controlled by the promoter of the erbin gene, X-gal activity in Erbin$_{1-693}$βgal should faithfully represent the expression of Erbin. To avoid possible effect of erbin mutation on the expression pattern of Erbin$_{1-693}$βgal, mammary glands were isolated from heterozygote erbin$^{+/\Delta C}$, instead of erbin$^{\Delta C/\Delta C}$, mice for analysis. erbin$^{+/\Delta C}$ mice did not exhibit any observable deficits in mammary gland structure or function (data not shown). X-gal in-situ assay revealed that the β-gal activity was detectable exclusively in mammary gland ducts but not in stromal cells (data not shown). Staining of cross sections indicated that β-gal activity was confined in luminal epithelial cells, but not in myoepithelial cells or in adipocytes (data not shown). These results corroborate that Erbin is specifically expressed in luminal epithelial cells of mammary glands.

Example 2

Erbin Regulation of Mammary Gland Development

Figure 1B:
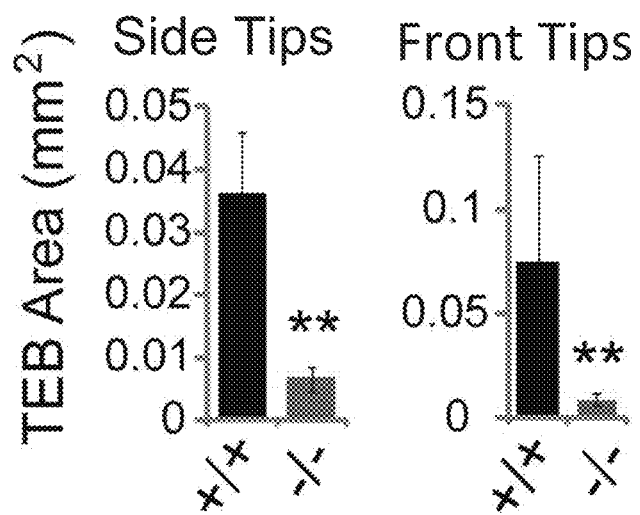
Figure 9:
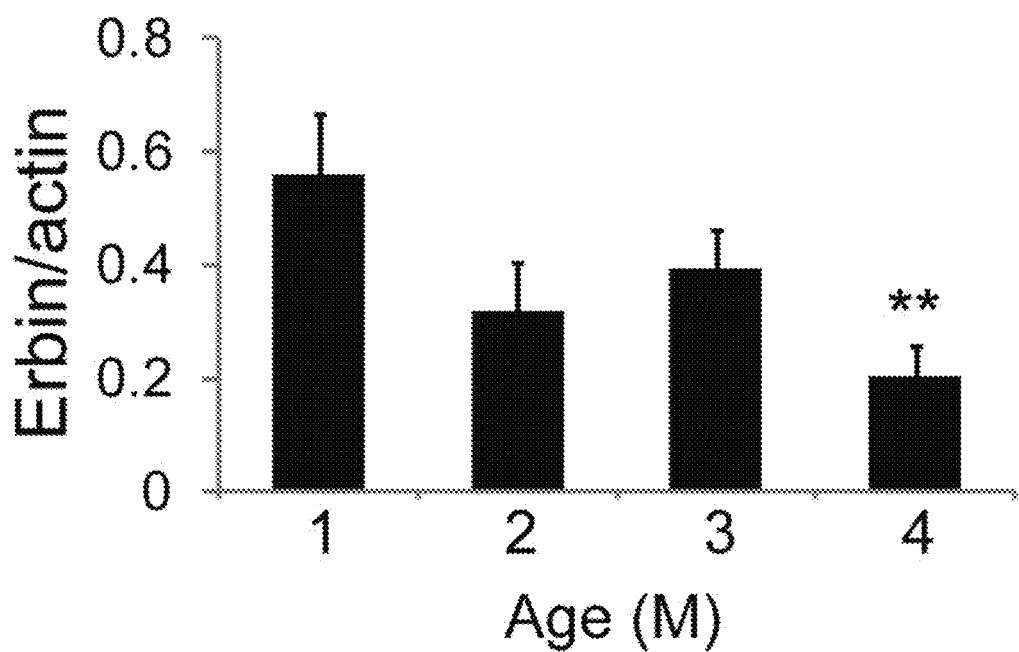
FIG. 9 shows the developmental expression of Erbin in mammary glands. Quantitative analysis of western blot data showing Erbin expression was higher at puberty and reduced afterwards. Mammary tissues were isolated from wild type or erbin$^{-/-}$ mice at different ages, homogenized and blotted for Erbin and β-actin. n=3, **P<0.01.

Mammary glands are initiated from nipples and extend at the onset of puberty due to active proliferation of epithelial cells (Hennighausen, L. et al. *Nature reviews* 6, 715-725, 2005). Interestingly, expression of Erbin in mammary glands is regulated during development. Erbin expression was highest in mice at one month of age and reduced in adult (FIG. 9). These results indicate a possible role of Erbin in the development of mammary glands. Mammary glands of wild type and erbin$^{-/-}$ C57B16 mice were compared at age of one month when puberty begins. The mouse forms five pairs of mammary glands. In wild type mice, ducts of mammary glands began to elaborate, with enlarged terminal end buds (TEBs) at the ends of individual tips (data not shown). In wild type mice, it was able to cover the area between the nipple and the LN at 4 weeks of age. In contrast, ducts of erbin$^{-/-}$ mammary glands were less elaborative with fewer and smaller TEBs (FIG. 1A and FIG. 1B). The tips of #4 gland reached only half way from the nipple to the LN. Because nipples were occasionally missed in dissection, it was difficult to quantify the distance between nipples and LNs. Therefore, the distance between the ductal tips to the LN were analyzed and found it was significantly increased from −0.31±1.09 mm in wild type to 3.70+0.68 mm in erbin$^{-/-}$ (n=4, P<0.01) (FIG. 1A). Moreover, the TEB area was reduced in erbin$^{-/-}$ mice (FIG. 1B).

Figure 1C:
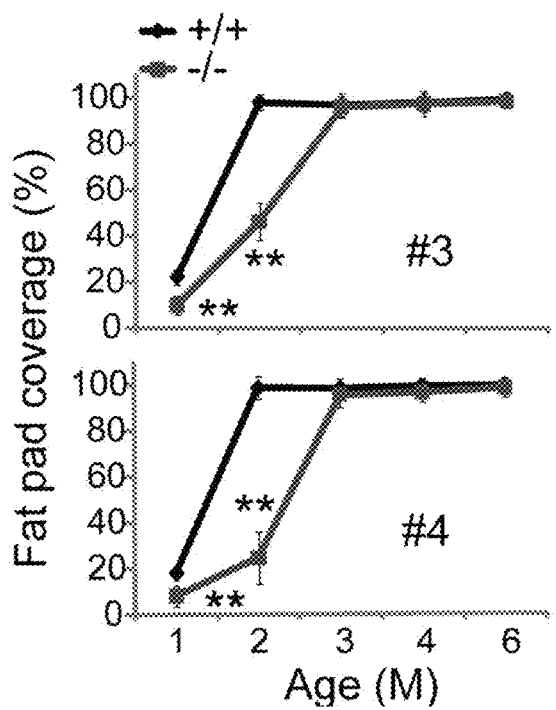
Figure 1D:
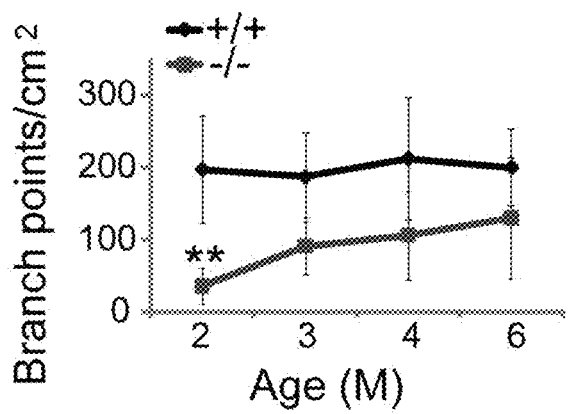

At 8 weeks of age, entire fat pads of #3 and #4 glands were nearly covered by elongated mammary ducts in the wild type mice (FIG. 1G). In contrast, only 20-40% of fat pad areas were covered by mammary ducts in erbin$^{-/-}$ mice (FIG. 1C and FIG. 1D). Moreover, the density of mammary ducts and branches in the covered area was significantly reduced in erbin$^{-/-}$ mice (FIG. 1C). The number of branch points was reduced in erbin$^{-/-}$, compared to that of control mice (FIG. 1D), indicating compromised complexity in ductal structure. These results indicate that Erbin may be necessary for development of mammary glands. Nevertheless, mammary ducts in erbin$^{-/-}$ fat pads appeared to extend with apparent TEBs at the tip of ducts (data not shown). By 3 months old of age or older, mammary ducts in erbin$^{-/-}$ mice were able to extend to cover entire fat pads (data not shown). The density of duct branches was similar between erbin$^{-/-}$ and wild type controls (data not shown). These results indicate that loss of Erbin delays, but does not abolish, the development of mammary glands. Similar delay in mammary gland development was observed in erbin$^{-/-}$ mice in different backgrounds including Balb/C and FVB (data not shown).

Example 3

Inhibition of Tumorigenesis In Vivo by Loss of Erbin

Deficient mammary gland development in erbin$^{-/-}$ mice intriguingly phenocopied the mice with conditional knockout of ErbB2 in mammary glands (Andrechek, et al. *Oncogene* 24, 932-937, 2005). Next, Erbin was investigated for whether or not it is necessary for breast cancer development in vivo. MMTV-neu mice express the rat homolog of ErbB2, neu, under the transcriptional control of the mouse mammary tumor virus (MMTV) promoter (Guy, C. T., et al., *PNAS*, 89, 10578-10582, 1992) and have served as a model for breast tumorigenesis (Muller, et al. *Cell*, 54, 105-115, 1988; Guy, C. T., et al., *PNAS*, 89, 10578-10582, 1992). Epithelial hyperplasia and alveola formation are thought to be pre-tumor stages induced by the oncogene in virgin mice (Andrechek, E. R., et al., *Cancer Res.*, 63, 4920-4926, 2003; Guy, C. T., et al., *Molecular and cellular biology*, 12, 954-961, 1992). To test this, mammary glands were harvested from adult virgin littermate female mice prior to development of visible tumor and whole-mount stained by hematoxylin. MMTV-neu; erbin$^{+/+}$ glands frequently showed epithelial hyperplasia, with significantly increased numbers of secondary and tertiary ductal branches (data not shown). However, in MMTV-neu; erbin$^{-/-}$ mice on the incipient congenic FVB background (5-generation backcrossing), ductal structures showed smooth contours and sometime slight alveolar formation, but without obvious epithelial hyperplasia. These results reveal that loss of Erbin prevented hyperplasia of mammary glands in MMTV-neu mice. On the incipient congenic FVB background, tumors were observed as early as 4 months of age in virgin MMTV-neu; erbin$^{+/+}$ mice, and by 18 months of age, 100% tumor incidence was observed for MMTV-neu; erbin$^{+/+}$ (FIG. 2A), in agreement with previous reports (Guy, C. T., et al., *PNAS*, 89, 10578-10582, 1992; Fantozzi, A. et al., *Breast Cancer Res.*, 8, 212, 2006; Rowse, G. J., et al., *Cancer Res.*, 58, 2675-2679, 1998). MMTV-neu overexpression induced focal tumors and hematoxylin and eosin (H & E) staining indicated typical adenocarcinoma morphology (data not shown). In mice that survive for two or more months after tumor onset, tumor metastasis was observed in the lung. Strikingly, MMTV-neu; erbin$^{-/-}$ mice failed to generate tumors that were detectable by anatomic examination within 20 months of age (FIG. 2A).

Figure 2B:
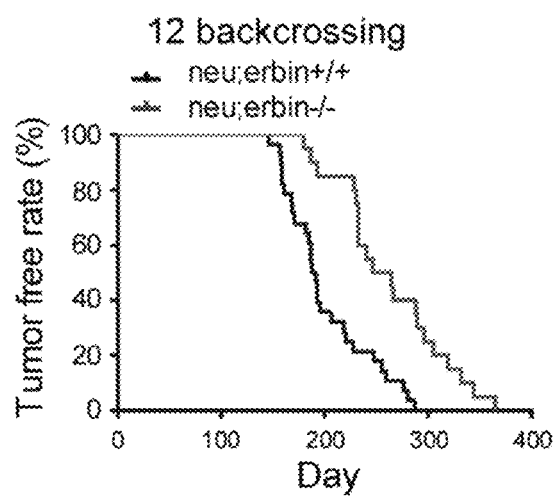
Figure 2C:
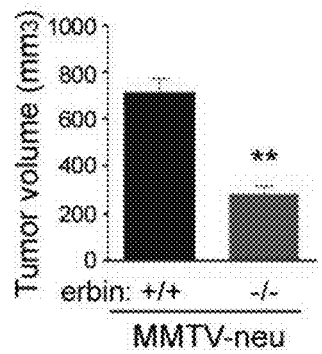

MMTV-neu; erbin$^{+/+}$ mice developed tumors at a faster rate than mice on congenic-FVB background (12-generation backcrossing), with 100% tumor incidence by 10 months of age (FIG. 2B). This observation was in agreement with previous reports that the FVB background favors breast tumor development in MMTV-neu mice (Rowse, G et al., *Cancer Res.*, 58, 2675-2679, 1998). However, the different genetic background had little effect in preventing Erbin mutation from inhibiting breast tumorigenesis. As shown in FIG. 2B, the tumor onset was significantly delayed in MMTV-neu; erbin$^{-/-}$ mice, compared to MMTV-neu; erbin$^{+/+}$. Histological examination of mammary glands did not show apparent difference in tumor pathology (data not shown). However, tumor volume was significantly smaller in MMTV-neu; erbin$^{-/-}$ mice, compared to MMTV-neu; erbin$^{+/+}$ five weeks after tumor onset (FIG. 2C), indicating the robust suppression of tumor growth by ablation of Erbin. Together, these observations indicate that mammary tumor development in MMTV-neu mice requires Erbin.

Figure 2D:
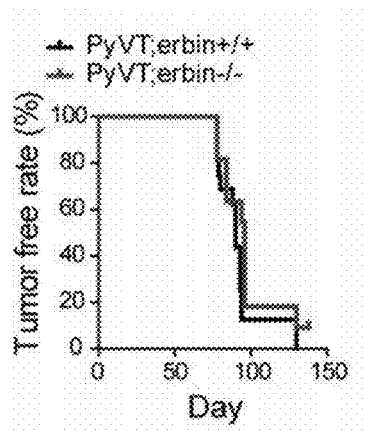
Figure 2E:
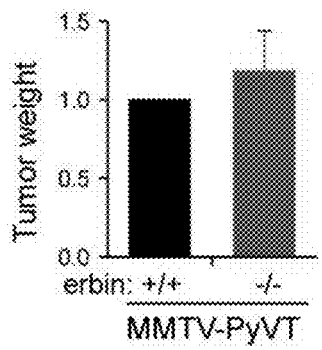

To determine whether Erbin regulation of breast tumorigenesis is specific for ErbB2-dependent tumors, erbin$^{-/-}$ mice were crossed with MMTV-PyVT mice that express the polyomavirus middle T antigen in mammary epithelial cells. MMTV-PyVT mice develop multi-focal tumors in early age with high incidence (Guy, et al., *Molecular and cellular biology*, 12, 954-961, 1992). Interestingly, loss of Erbin had no effect on rate of tumor incidence, at ages when tumors began to occur, or on tumor weight (FIGS. 2D and 2E). Histological examination indicated that breast tumors in MMTV-PyVT were highly fibrotic, as previously reported (Guy, et al., *Molecular and cellular biology*, 12, 954-961, 1992), which was not altered by erbin mutation (data not shown). These results indicate that Erbin ablation has no effect on breast tumorigenesis due to overexpression of the polyomavirus middle T antigen in mammary epithelial cells. Together with results from MMTV-neu mice, these observations indicate that Erbin is specifically required for ErbB2-dependent tumorigenesis.

Example 4

Requirement of Erbin for ErbB2-Dependent Growth of Breast Cancer Cells

Figure 3A:
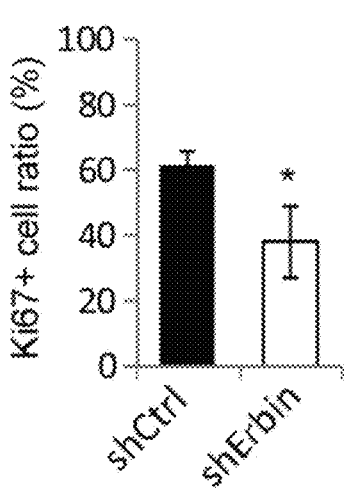
FIGS. 3A-3D show that Erbin promotes ErbB2-dependent proliferation. (A) Quantitative analysis of data in [[a]] (A). n=3, *P<0.05, compared to shCtrl. (B) Erbin knock-down reduced expression of Erbin and ErbB2 in MCF10A cells. MCF10A cells were infected with shCtrl or shErbin lentivirus and purified by FACS, to yield shCtrl- or shErbin-infected MCF10A cells. They were subsequently transfected with Flag-tagged ErbB2/pcDNA3.1 and selected with G418 to yield shCtrl-B2 and shErbin-B2 cells. Lysates were blotted for Flag, Erbin, or β-actin. ErbB2 levels were lower in shErbin-B2 MCF10A cells in comparison with shCtrl-B2 cells. (C)-(D) Erbin reduction suppressed ErbB2-dependent proliferation in an in vitro DCIS model. Cells described in c were grown in Matrigel 3D cultures. Shown were phase (C) Reduced size in acinar structure by shErbin. Size was normalized by shCtrl cells. n>3. P<0.01, compared to shCtrl; $^{\#\#}$P<0.01, compared to shCtrl-B2. (D) Reduced Ki67-positive cell ratio by shErbin. n>3, P<0.01, compared to shCtrl; $^{\#}$P<0.05, compared to shCtrl-B2.
Figure 10A:
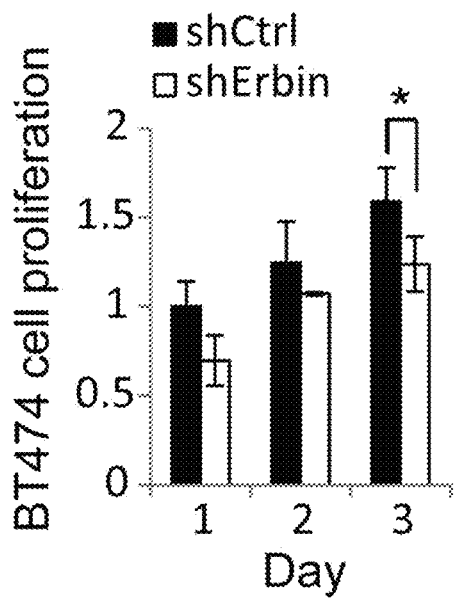
FIGS. 10A, 10B, and 10C show the depletion of Erbin inhibited proliferation of ErbB2-dependent breast cancer cells. shErbin suppression of cell growth of ErbB2-dependent, but not ErbB2-independent breast cancer cells. BT474 (A), SKBR3 (B), ZR751 (C) cells were infected with shCtrl or shErbin lentivirus and sorted by FACS. Cell growth was monitored by MTS assay. n=3, *P<0.05, **P<0.01.
Figure 10B:
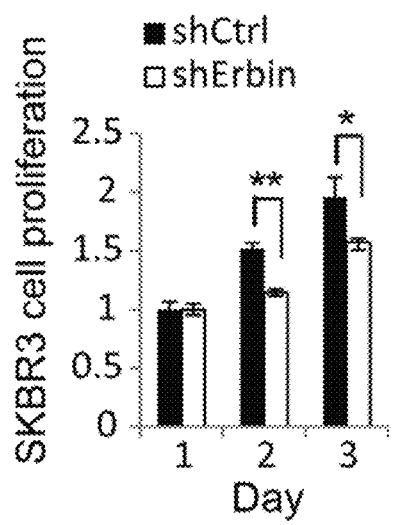
Figure 10C:
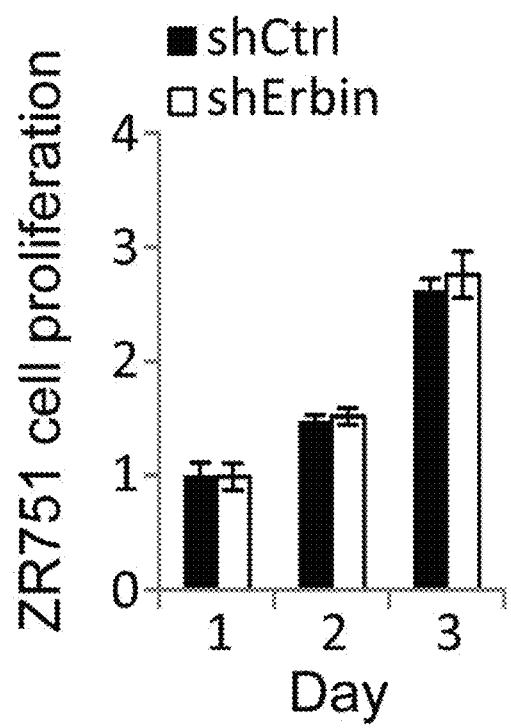

Given that Erbin is necessary for ErbB2-dependent tumor generation and growth, ErbB2-dependent proliferation of breast cancer cells was investigated. SKBR3 cells, whose proliferation are dependent on high levels of ErbB2 (Neve, et al., *Cancer cell*, 10, 515-527, 2006; Kao, et al., *Genes, chromosomes & cancer*, 45, 761-769, 2006), were infected with lentivirus encoding Erbin shRNA (shErbin) or scrambled sequence (shCtrl) and stained for nuclear proliferation marker, Ki67 (Brantley-Sieders, D. M., et al., *The Journal of clinical investigation*, 118, 64-78 (2008). Ki67-positive cells were significantly reduced in shErbin virus-infected cells (identified by viral GFP) (FIG. 3A), supporting the notion that Erbin depletion suppresses the proliferation of ErbB2-overexpressing cancer cells. To test this further, SKBR3 and BT474 cells, both of which are ErbB2-dependent (Neve, R. M., et al., *Cancer cell*, 10, 515-527, 2006; Kao, J. et al., *Genes, chromosomes & cancer*, 45, 761-769, 2006), were infected by lentiviral shRNA and sorted by FACS for GFP to establish stable cell lines. Levels of Erbin were reduced in shErbin-infected cells by 70-90%, compared to those with shCtrl (data not shown). Intriguingly, the numbers and viability of shErbin-BT474 and shErbin-SKBR3 cells were significantly reduced by days 2 or 3 of plating, compared to shCtrl-infected cells (FIGS. 10A and 10B), confirming that Erbin may be necessary for ErbB2-dependent proliferation of breast cancer cells. As a control, Erbin knockdown had little effect on the proliferation of ZR751 cells, a breast cancer cell line whose growth depends on the estrogen receptor but not ErbB2 (Neve, R. M., et al., *Cancer cell*, 10, 515-527, 2006) (FIG. 10C). These results indicate that Erbin is necessary for ErbB2-dependent proliferation of breast cancer cells.

Figure 3B:
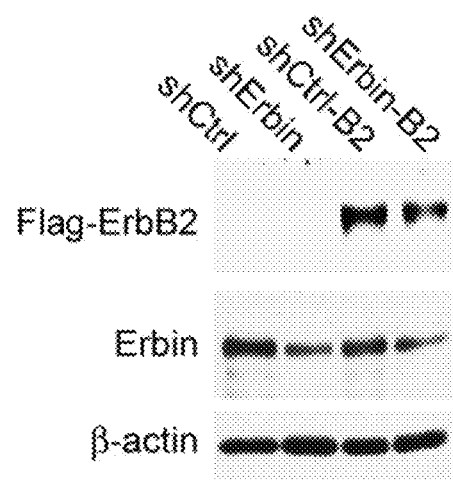
Figure 3C:
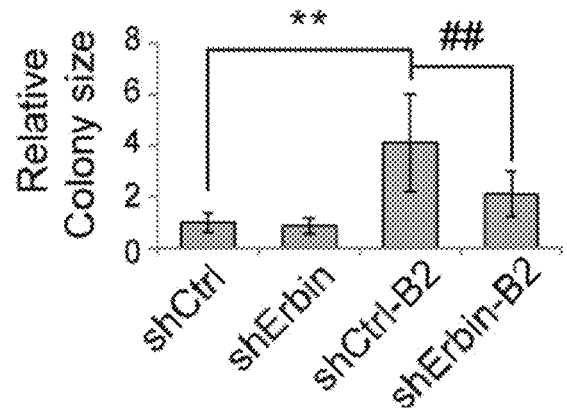
Figure 3D:
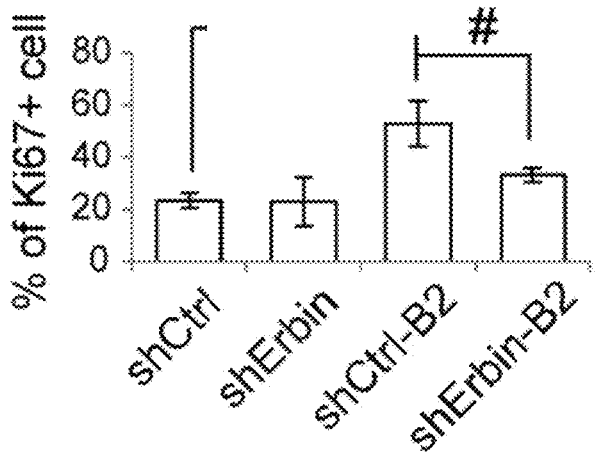
Figure 11A:
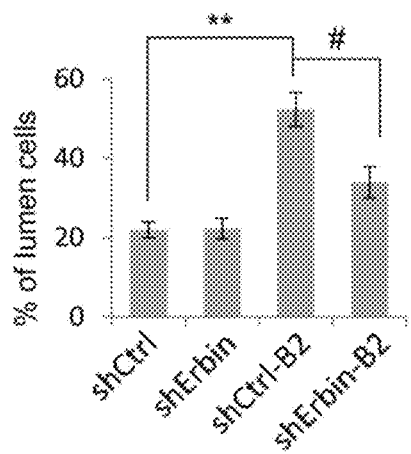
FIGS. 11A and 11B show that Erbin is required for ErbB2-dependent lumen invasion of epithelial cells. (A) Quantitative analysis of data showing ErbB2-dependent lumen filling was blocked by lentiviral shErbin. MCF10A cells were infected with shCtrl or shErbin lentivirus and purified by FACS to yield MCF10A cells expressing shCtrl or shErbin. Some cells were subsequently transfected with Flag-tagged ErbB2/pcDNA3.1 and selected with G418 to yield shCtrl-B2 and shErbin-B2 cells. shCtrl, shErbin, shCtrl-B2 and shErbin-B2 cells were cultured in Matrigel for 14 days to form acini or multi-acini structures. Shown are representative images of single acini of indicated cells. Acinar structures were stained with DAPI and images were captured by a confocal microscope. Notice that ErbB2-overexpression (as shCtrl-B2) caused disorganization of luminal structure and filling of lumens with extra cells. These effects of ErbB2 were inhibited by shErbin (as in shErbin-B2). **P<0.01, compared to shCtrl; #P<0.05, compared to shCtrl-B2. (B) Effect of Erbin on proliferation of normal breast epithelial cells. MCF10A cells stably expressing shCtrl or shErbin were examined for proliferation by MTS assay.
Figure 11B:
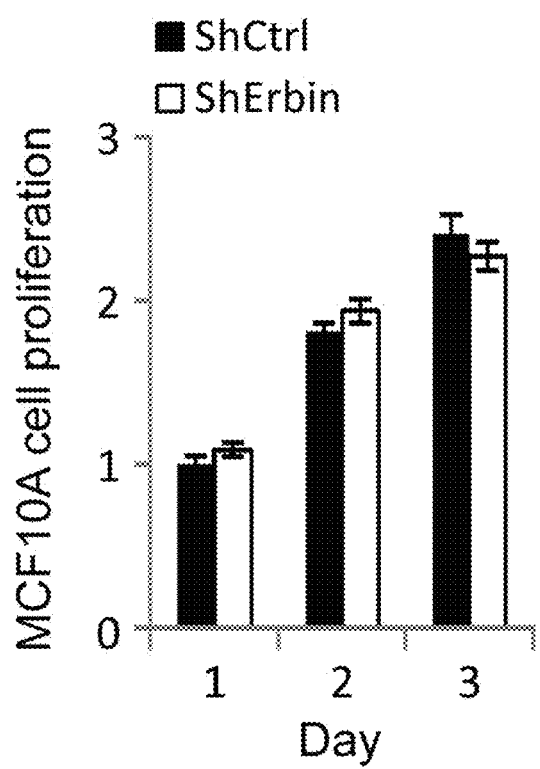

ErbB2 is frequently overexpressed at the onset of ductal carcinoma in situ (DCIS) in patients (Nofech-Mozes, et al., *Advances in anatomic pathology*, 12, 256-264, 2005; van de Vijver, M. J., et al, *The New England journal of medicine*, 319, 1239-1245, 1988). Next, MCF10A, a nontransformed human mammary epithelial cell line, was used which was infected with viral shErbin or shCtrl and sorted for GFP expression. shErbin-infected cells were subsequently transfected with N-terminal Flag-tagged ErbB2 or empty vector together with pcDNA3.1 (10:1 ratio) and selected by G418 resistance (FIG. 3B). When cultured on Matrigel, MCF10A cells formed acini-like structures with a single layer of polarized, growth-arrested cells and lumen in the center (FIGS. 11A and 11B), in agreement with previous studies (Muthuswamy, et al., *Nature cell biology* 3, 785-792, 2001). MCF10A cells expressing ErbB2 (shCtrl-B2), but not shCtrl-MCF10A, were able to form multiacini-like structures (data not shown). Moreover, ErbB2 expression also increased the number of Ki67-positive cells (shCtrl-B2 versus shCtrl) and the number of cells in the luminal space (FIG. 3D and FIG. 11A). Erbin reduction in naive MCF10A cells, shown in FIG. 3b, had little effect on the size of acini-like structures, nor the number of Ki67-positive cells (FIGS. 3C and 3D), nor the proliferation (FIG. 11B). In contrast, the reduction of Erbin prevented ErbB2 from increasing the size of acini-like structures, the number of Ki67-positive cells, and the number of cells in the luminal space (FIGS. 3C and 3D and FIG. 11). Note that cells that intruded into the lumen were GFP-negative (i.e., Erbin expression was not suppressed) (data not shown), indicating that Erbin depletion inhibits ErbB2-dependent lumen invasion of cells. These results indicate Erbin is required for ErbB2-dependent carcinogenesis in an in vitro DCIS model.

Example 5

Promotion of ErbB2 Stability by Erbin

Figure 4A:
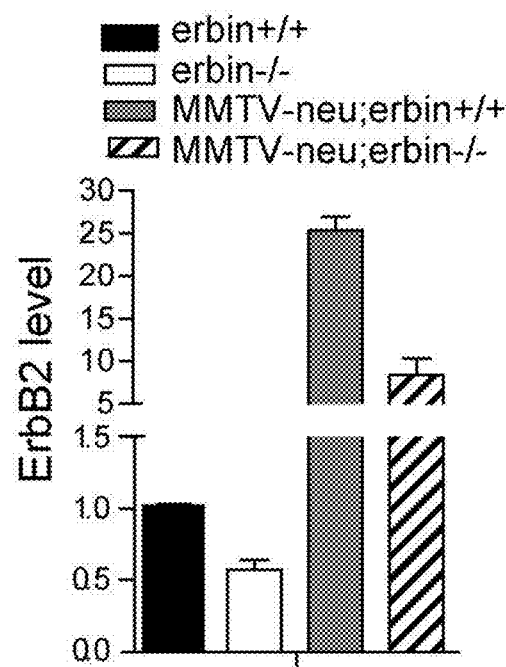
FIGS. 4A-4E show that Erbin promotes ErbB2 stability, homodimerization and autophosphorylation. (A) Quantitative analysis of ErbB2 in breast tissues in a. n=3. **P<0.01. (B) shErbin had no effect on ErbB2 mRNA levels in breast cancer cells. Total RNA was extracted from stable cells expressing shCtrl or shErbin and subjected for ErbB2 by real time RT-PCR. Results were normalized to internal control α-tubulin in each sample. (C) Quantitative analysis of western blot data showing Erbin is required for ErbB2 stabilization in breast cancer cells. BT474 cells were infected with lentiviral shCtrl or shErbin and sorted by FACS. Cells were treated by cycloheximide (CHX, 50 µM) for indicated times and analyzed for endogenous ErbB2 by Western blot. n=3, *P<0.05, **P<0.01, compared to shCtrl. (D) Quantitative analyses of western blot data showing Erbin enhances autophosphorylation of ErbB2 in the absence of neuregulin. HEK293 cells were co-transfected with Myc-Erbin and Flag-ErbB2, lysed and blotted for ErbB2 and phosphorylated pErbB2. n=3, *P<0.05. (E) Quantitative analysis of western blot data showing that Erbin promotes ErbB2 homodimerization and that Erbin has no effect on ErbB2/ErbB3 heterodimerization. For the homodimerization studies, HEK293 cells were transfected with Myc-ErbB2, Flag-ErbB2, or HA-Erbin, respectively. Lysates containing Myc-ErbB2 and Flag-ErbB2 were mixed together with or without HA-Erbin and then subjected to precipitation with anti-Flag antibody. Resulting complexes were probed with indicated antibodies. For the heterodimerization studies, HEK293 cells were transfected with ErbB3, Flag-ErbB2, or HA-Erbin, respectively. Lysates containing ErbB3 and Flag-ErbB2 were mixed together with or without HA-Erbin and then subjected to precipitation with anti-Flag antibody. Resulting complexes were probed with indicated antibodies. n=3, *P<0.05.

The in vitro and in vivo data indicate that Erbin is critical for ErbB2-dependent proliferation and transformation of mammary epithelial cells and for tumorigenesis in MMTV-neu mice. Next, underlying mechanisms by which Erbin ablation suppresses ErbB2-dependent tumor development were investigated. First, the expression of Erbin and ErbB2 levels in tumors and mammary glands in MMTV-neu or control mice were examined. As shown in FIG. 4A, ErbB2 levels in breast tumors of MMTV-neu mice were higher than those in control erbin$^{+/+}$ mice, in agreement with previous reports (Guy, C. T., et al., 89, 10578-10582, 1992). Also increased in breast tumors of MMTV-neu mice were levels of other ErbB members including EGFR, ErbB3 and ErbB4, but not the ligand neuregulin 1 (NRG1). Interestingly, Erbin expression was significantly elevated (by 2.6±0.6 folds above control) in MMTV-neu-induced tumors. The correlated expression of Erbin and ErbB2 is in support of the notion that Erbin promotes ErbB2 function. To test this hypothesis further, the levels of ErbB2 in erbin$^{-/-}$ mice were examined. There was a mild reduction in ErbB2 levels, but not of EGFR, ErbB3 or ErbB4, in control mice by Erbin ablation (data not shown). However, Erbin loss caused a dramatic decrease in ErbB2 levels in MMTV-neu mammary glands (from 25.4±0.4 to 8.4±1.9 folds above control in erbin$^{+/+}$ and erbin$^{-/-}$, respectively, n=3, P<0.05). These observations demonstrate a positive correlation between levels of Erbin versus ErbB2 and ErbB2-induced proliferation and tumorigenesis.

Figure 4B:
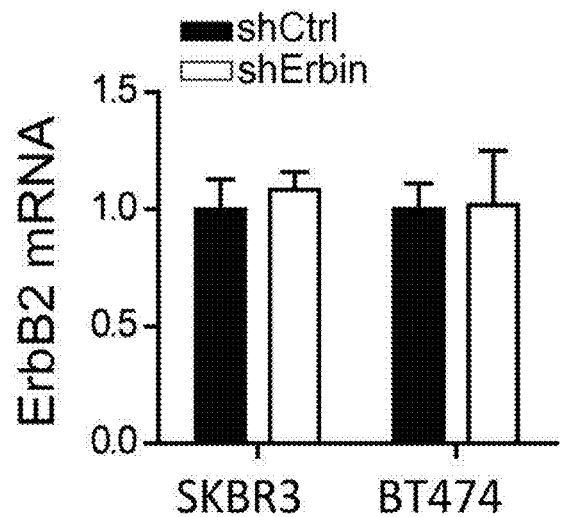

EGFR, ErbB3, and ErbB4 levels in MMTV-neu; erbin$^{-/-}$ mammary tissues are similar to those in control mice (data not shown). The increase in EGFR, ErbB3, and ErbB4 in MMTV-neu-induced tumors (data not shown) may be secondary to enhanced ErbB2 signaling or tumor progression (Siegel, et al., *The EMBO journal*, 18, 2149-2164, 1999). To identify its primary target, Erbin expression was suppressed in BT474 breast cancer cells and probed for different ErbBs. Levels of ErbB2, but not EGFR or ErbB3, were reduced in BT474 cells by Erbin knockdown, identifying ErbB2 as a primary target (data not shown). In agreement, Erbin knockdown reduced ErbB2 levels on cell surface (data not shown). Conversely, ErbB2 levels were increased in a manner dependent on Erbin concentration in transfected cells (data not shown). Finally, Erbin reduction did not appear to alter levels of ErbB2 mRNA (FIG. 4B). Together, these results indicate that Erbin can regulate ErbB2 protein levels by a posttranscriptional mechanism. The ability of Erbin to alter ErbB2 stability was tested. BT474 cells were treated with cycloheximide (CHX) to inhibit protein synthesis and analyzed for ErbB2 expression. Depletion of Erbin expedited ErbB2 degradation (FIG. 4C), with half-life reduced from ~9 hours in shCtrl-expressing cells to ~4.5 hours in shErbin-expressing breast cancer cells (n=3, P<0.05). This result indicates that ErbB2 is more stable in the presence of Erbin but undergoes rapid degradation when Erbin is reduced in breast cancer cells, consistent with an earlier study of Erbin in HEK293 and Schwann cells (Tao, Y., et al., *PNAS*, 106, 9477-9482, 2009). Together, these results indicate that Erbin maintains ErbB2 levels in breast cancer cells by stabilizing the protein. It was also shown that knock-down of Erbin promoted ErbB2 ubiquitination. (data not shown).

Erbin regulation of ErbB2 stability was investigated. ErbB2 is the client of HSP90 and inhibition of HSP90 by 17-AAG, which dissociates the HSP90 complex, had no effect on Erbin levels, but resulted in ErbB2 degradation (data not shown), partially via the ubiquitination-proteasome pathway (Zhou, P., et al., *The Journal of biological chemistry*, 278, 13829-13837, 2003; Xu, W., et al., *The Journal of biological chemistry*, 276, 3702-3708, 2001; Xu, W., et al., *Cell stress & chaperones*, 7, 91-96, 2002). Intriguingly, the effect of 17-AAG could not be blocked by Erbin overexpression (data not shown), indicating Erbin acts upstream or at level of HSP90. ErbB2, HSP90, and Erbin can form a ternary complex necessary for ErbB2 stability. HSP90 as well as Erbin was detectable in the complex of ErbB2 and Erbin interacted HSP90 (data not shown). Brief treatment (1 hour) with 17-AAG inhibits HSP90 without altering ErbB2 level, which is known to inhibit the ErbB2-HSP90 association (Xu, et al., *Molecular and cellular biology*, 27, 220-228, 2007) (data not shown). Intriguingly, the amount of Erbin in the ErbB2 complex was also reduced, indicating that HSP90 facilitates the Erbin-ErbB2 association. Conversely, Erbin knockdown inhibited the HSP90-ErbB2 interaction (data not shown). These results are in support a ternary complex and indicate that Erbin regulates ErbB2 stability by promoting the interaction between HSP90 and ErbB2.

Example 6

Enhancement of ErbB2 Activity by Erbin

Figure 4C:
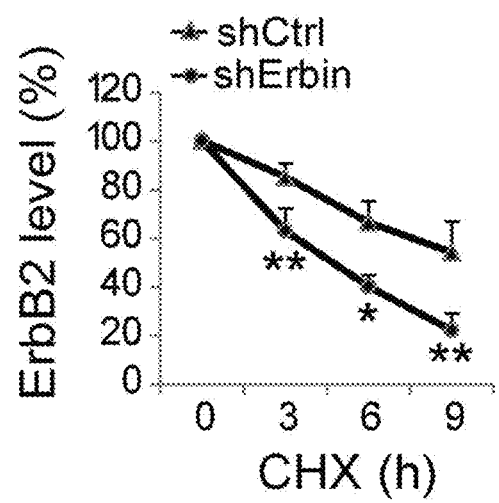
Figure 4D:
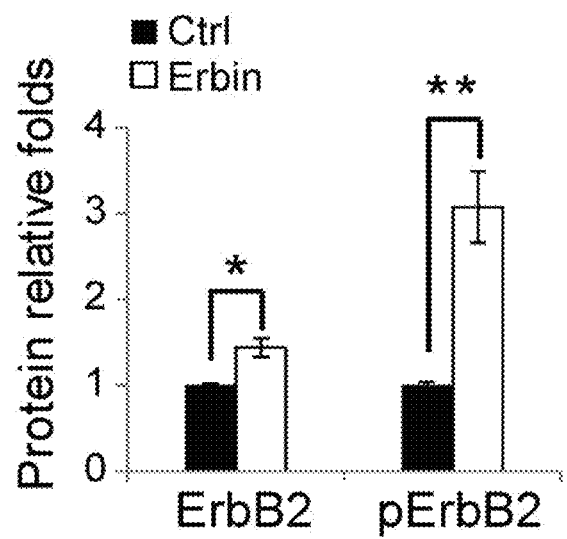
Figure 4E:
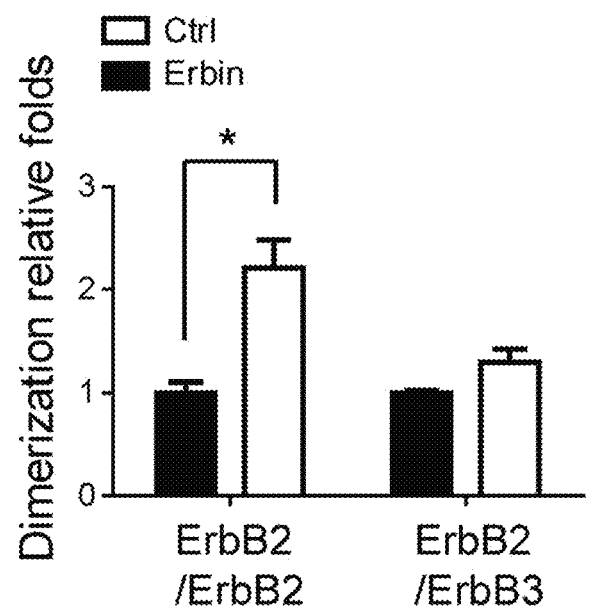
Figure 12A:
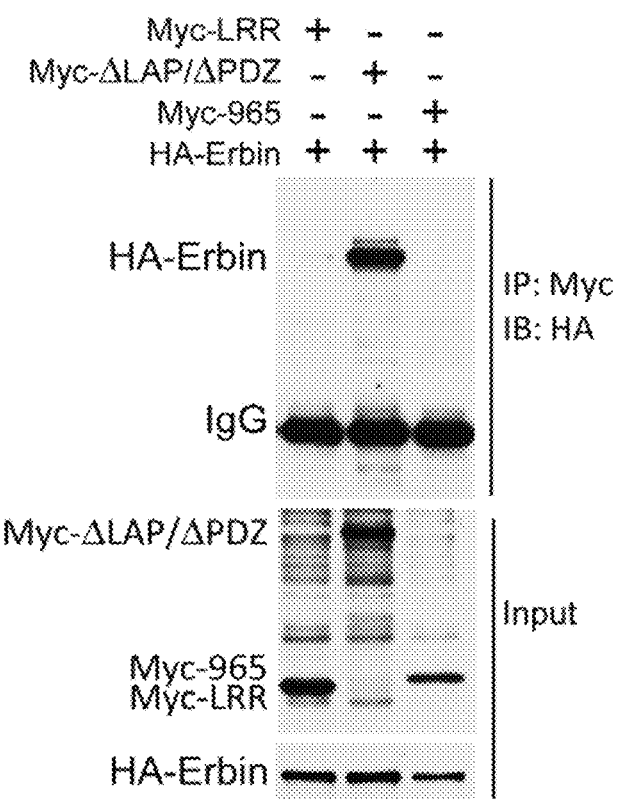
FIGS. 12A and 12B show the identification of the domain in Erbin potentially involved in its dimerization. (A) HEK293 cells were transfected with HA-Erbin and one of the Myc-Erbin truncation mutants: Myc-LRR, Myc-ΔLAP/ΔPDZ or Myc-965. Lysates were subjected to precipitation with anti-Myc antibody. Resulting complexes were probed with anti-HA antibody. HA-Erbin was specifically present in precipitates of Myc-ΔLAP/ΔPDZ. (B) Schematic diagrams of Erbin domain structure and binding activity.
Figure 12B:
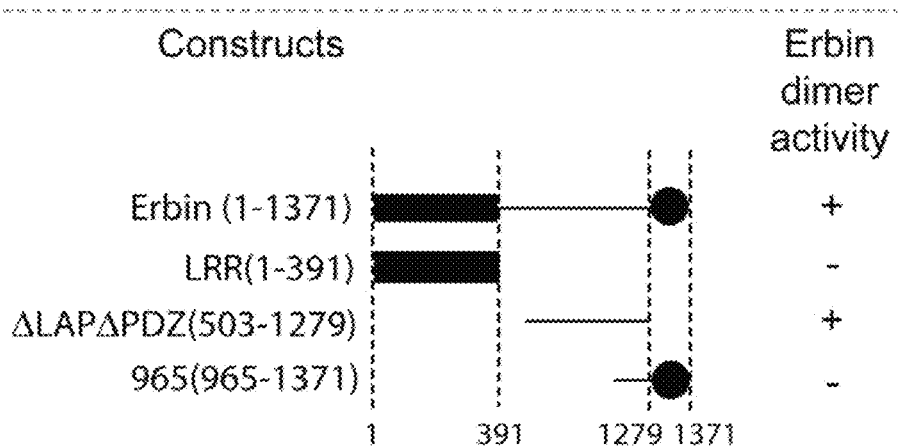

To determine if Erbin regulates ErbB2 signaling, changes in ErbB2 levels were investigated to determine if they parallel its tyrosine phosphorylation, an indication of its activation (Yarden, et al., *Nat. Rev. Cancer*, 12:553-563, 2012). HEK293 cells were transfected with ErbB2 alone or together with Erbin and characterized for ErbB2 and phosphorylated ErbB2 (pErbB2). As expected, ErbB2 levels increased in Erbin-expressing cells, compared to cells not transfected with Erbin. Concomitantly, pErbB2 was enhanced. Notably, the increase in pErbB2 was disproportionally larger than that in ErbB2 levels (3.1±0.4 folds versus 1.4±0.1 folds, respectively, n=4, P<0.05) (FIG. 4D). This result indicates that Erbin can also enhance ErbB2 activity, in addition to stability. ErbB2 overexpressed in tumor cells is known to form homodimers and become autophosphorylated, and thus escapes from ligand regulation (Muthuswamy, et al., *Nature cell biology*, 3, 785-792, 2001; Worthylake, R., et al., *JBC*, 274, 8865-8874, 1999; Di Fiore, P. P., et al., *Science*, 237, 178-182, 1987; Di Marco, et al., *Molecular and cellular biology*, 10, 3247-3252, 1990; Samanta, A., et al., *PNAS*, 91, 1711-1715, 1994). This is thought to be a mechanism for overexpressed ErbB2 to promote breast tumorigenesis and malignancy. Erbin can promote ErbB2 dimerization and thus increase its autophosphorylation. N-terminal Myc- and Flag-tagged ErbB2 were generated and the effect of Erbin on their dimerization was examined. Cells expressing Myc-ErbB2 or Flag-ErbB2 were lysed and respective lysates were incubated in the presence or absence of Erbin. Flag-ErbB2 co-precipitated with Myc-ErbB2, indicating dimerization (data not shown). Intriguingly, the amount of Myc-ErbB2 associated with Flag-ErbB2 was increased (by 2.2±0.3 folds) by Erbin (FIG. 4C). This result indicates that Erbin enhances ErbB2 homodimerization. This effect is specific for ErbB2 because Erbin had no effect on the heterodimerization of ErbB2 and ErbB3 (FIG. 4C). Each Erbin molecule has one binding domain for ErbB2 (Borg, J. P., et al., *Nature cell biology*, 2:407-414, 2000; Huang, Y. Z., et al., *JBC*, 276:19318-19326, 2001). To investigate how Erbin promotes ErbB2 homodimerization, the ability of Erbin itself to form homodimers was determined. Myc-tagged and HA-tagged Erbin were transfected into HEK293 cells and ensuing lysates were subjected to co-precipitation. Notably, abundant amounts of HA-Erbin were detected in the complex of Myc-Erbin (data not shown). The association of HA-Erbin with Myc-Erbin was specific because HA-Erbin was not precipitated by anti-Myc antibody from cell lysates without Myc-Erbin (data not shown). These results demonstrate that Erbin was able to form homodimers in cells, providing a mechanism of inducing ErbB2 dimerization. Domain mapping experiments indicate that Erbin dimerization can involve a region between aa 503-965, but not the LRR or PDZ domain (FIGS. 12A and 12B).

Example 7

A Critical Role for the Erbin-ErbB2 Interaction

Erbin PDZ Disrupts the Erbin ErbB2 Interaction and Reduces ErbB2 Levels and Phosphorylation (Activity)

Figure 5A:
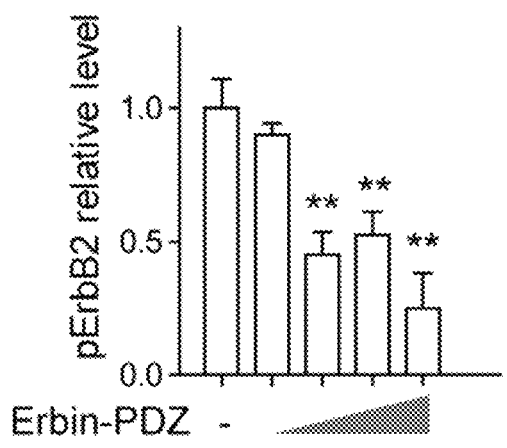
FIGS. 5A-5H show the requirement of the Erbin-ErbB2 interaction for ErbB2 stabilization and autophosphorylation and ErbB2-dependent proliferation of breast cancer cells. (A)-(B) Quantitative analysis of pErbB2 and ErbB2 levels in western blots showing decreased ErbB2 expression and autophosphorylation by Erbin-PDZ domain. HEK293 cells were transfected with Flag-ErbB2 with increasing doses of Myc-Erbin-PDZ. Cell lysates were blotted with antibodies against ErbB2, pErbB2 and Myc. (C) Quantitative analysis of western blot data showing the disruption of the Erbin-ErbB2 interaction by B2tail. Lysates of transfected cells expressing Flag-ErbB2 or Myc-Erbin were incubated with control peptide (Ctrl) or B2tail. The Erbin complex was precipitated using anti-Myc antibody and probed for ErbB2. n=3, *P<0.05, compared to Ctrl. (D) Quantitative analysis of data from the treatment of breast cancer cells with TAT-B2tail which shows a decrease in ErbB2 stability and pErbB2. SKBR3 cells were incubated with 20 µM TAT-Ctrl or TAT-B2tail, for 1 hour prior to analysis of ErbB2 stability. n=3, *P<0.05, **P<0.01, compared to TAT-Ctrl. (E) TAT-B2tail treatment inhibits proliferation of SKBR3 and BT474 cells. Cells were treated with 20 µM TAT-Ctrl or TAT-B2tail peptide for 24 hours and analyzed by MTS assay. (F)-(H) Show that the Erbin PDZ domain is necessary for ErbB2-dependent tumorigenesis in vivo. (F) PDZ deletion inhibited tumorigenesis in MMTV-neu mice on incipient congenic FVB background. Erbin$^{\Delta C/\Delta C}$ mice were backcrossed for 5 generations with FVB wild types and then crossed with FVB-congenic MMTV-neu. Virgin littermates of MMTV-neu; erbin$^{\Delta C/\Delta C}$ and MMTV-neu; erbin$^{+/+}$ mice (n=20 and 22, respectively) were examined for tumor by weekly palpation. Kaplan-Meier survival plot. Log-rank (Mantel-Cox) test, P<0.0001. (G)-(H) PDZ deletion had no effect on tumorigenesis in MMTV-PyVT mice. Virgin littermates of MMTV-PyVT; erbin$^{+/+}$ (n=23) and MMTV-PyVT; erbin$^{\Delta C/\Delta C}$ (n=15) mice were examined for tumor by weekly palpation. (G) Kaplan-Meier survival plot. Log-rank (Mantel-Cox) test, P=0.595. (H) PDZ deletion had no effect on breast tumor growth in MMTV-PyVT mice. n=8, P>0.05.
Figure 5B:
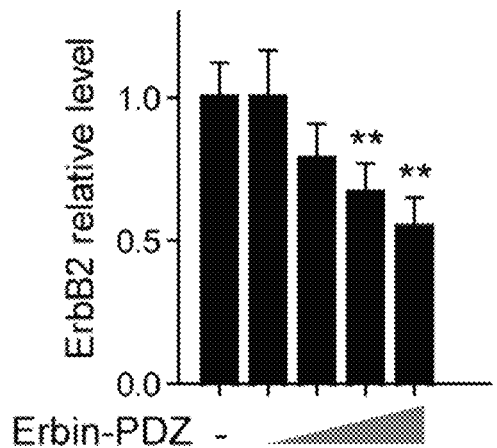
Figure 5C:
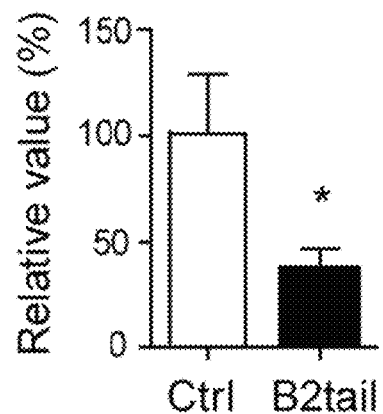

Erbin is known to interact with ErbB2 (Borg et al., 2000; Huang et al., 2001). This interaction requires the C-terminal region of ErbB2 and the PDZ domain of Erbin. To determine if the interaction is required for Erbin regulation of ErbB2 stability and activity, the consequence of overexpression of Erbin and ErbB2 domains that are sufficient for interaction were explored. These domains may serve as a dominant negative inhibitor of the Erbin-ErbB2 interaction. HEK293 cells were transfected with Flag-ErbB2 alone or together with full length Erbin. Full length Erbin increased ErbB2 levels and phosphorylation. However, coexpression of the PDZ domain of Erbin reduced the levels of ErbB2 and its phosphorylation (FIGS. 5A and 5B), indicating that the Erbin-ErbB2 interaction is necessary for Erbin regulation. B2tail Disrupts the Erbin-ErbB2 Interaction and Reduces ErbB2 Levels and Activity in Breast Cancer Cells B2tail, a peptide that contains the C-terminal 15 amino acid residues of ErbB2 and is sufficient to interact with Erbin, was generated (Huang et al., 2001). B2tail was able to disrupt the Erbin-ErbB2 interaction in vitro (FIG. 5C). To facilitate cell membrane penetrance, a B2tail peptide containing an additional 12 amino acid residues of the transactivator of transcription (TAT) of human immunodeficiency virus (Schwarze et al., 1999) was generated. To test its penetrating efficiency, the TAT peptide was conjugated with fluorescein-5-isothiocyanate (FITC) and TAT-FITC was used to treat SKBR3 cells.

Figures 1, 5D:
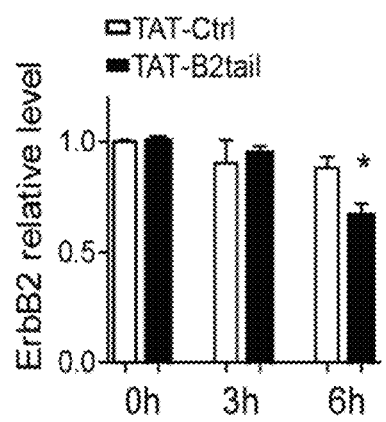
Figures 2, 5D:
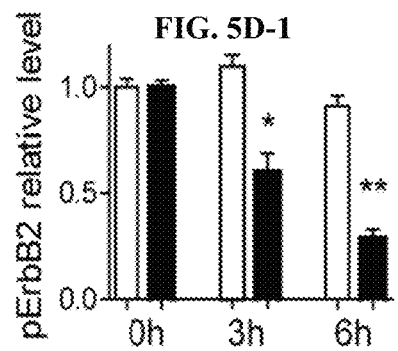
Figure 5E:
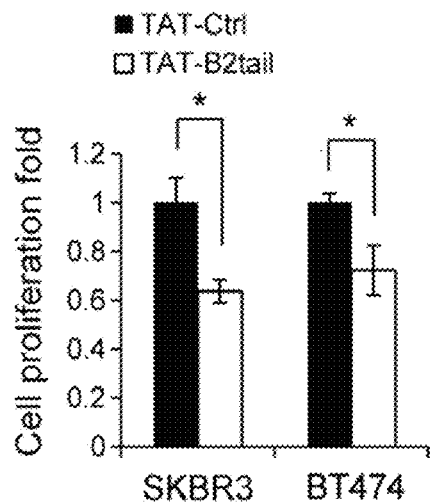

SKBR3 cells were treated with 20 pM TAT-B2tail for 1 hour prior to the addition of CHX to inhibit protein synthesis. As shown in FIG. 5D, ErbB2 reduction was faster in TAT-B2tail-treated cells, compared to cells treated with TAT-Ctrl peptide (scrambled). Accordingly, pErbB2 levels were reduced in TAT-B2tail-treated cells compared to cells treated with TAT-Ctrl (FIG. 5D).
B2tail Inhibits ErbB2-Dependent Proliferation of Breast Cancer Cells Incubating with TAT-B2tail, but not control peptides, significantly decreased proliferation of SKBR3 and BT474 cells by about 40% and 35%, respectively (FIG. 5E). This result indicates that disruption of the Erbin-ErbB2 interaction increases the degradation of ErbB2, reduces ErbB2 signaling and inhibits ErbB2-dependent proliferation.

Example 8

Requirement of Erbin PDZ Domain for Tumorigenesis in MMTV-Neu Mice

Figure 5F:
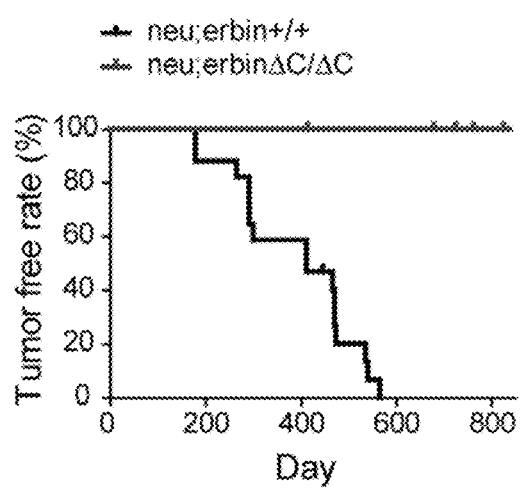
Figure 5G:
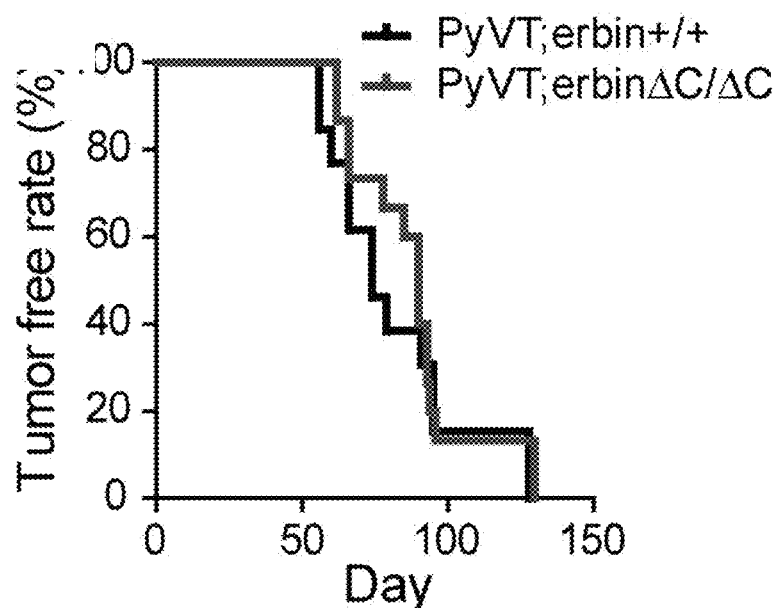
Figure 5H:
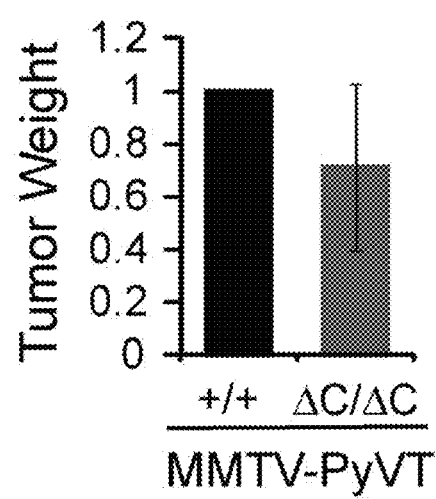

To investigate whether the interaction between Erbin and ErbB2 is crucial for breast tumorigenesis and progression in vivo, MMTV-neu mice were crossed with erbin$^{\Delta C/\Delta C}$ mice. As described above, erbin$^{\Delta C/\Delta C}$ mice express Erbin$_{1-693}$βgal that lacks 694-1450 amino acid residues of mouse Erbin in the C-terminus including the PDZ domain. Thus, Erbin$_{1-693}$βgal is unable to interact with ErbB2 (Huang, Y. Z., et al., *JBC*, 276:19318-19326, 2001) (data not shown). At the fifth generation of backcrossing into FVB background, MMTV-neu; erbin$^{\Delta C/\Delta C}$ mice resembled almost all pheno types observed in MMTV-neu; erbin$^{-/-}$ mice. No tumor incidence was observed in MMTV-neu; erbin$^{\Delta C/\Delta C}$ within 20 months of age (FIG. 5F). H & E staining of sections of mammary fat pads or lungs from MMTV-neu; erbin$^{\Delta C/\Delta C}$ mice revealed no focal or metastatic tumors (data not shown). These results indicate that the C-terminal region of Erbin including the PDZ domain is necessary for mammary tumor development in MMTV-neu mice, in agreement with results of in vitro studies. Also as observed in MMTV-neu; erbin$^{-/-}$ mice, MMTV-neu; erbin$^{\Delta C/\Delta C}$ mammary glands showed no obvious epithelial hyperplasia (data not shown), indicating that the C-terminal region of Erbin is required for ErbB2-driven epithelial proliferation. Finally, multi-focal, fibrotic tumors were observed in MMTV-PyVT; erbin$^{\Delta C/\Delta C}$ at similar rate and size as those in MMTV-PyVT; erbin$^{+/+}$ (data not shown), indicating that deletion of the C-terminal region in Erbin had no effect on breast tumorigenesis due to overexpression of the polyomavirus middle T antigen in mammary epithelial cells. Together, these results demonstrate a critical role for Erbin's C-terminal region in promoting ErbB2-dependent tumorigenesis and indicate a working model where Erbin regulates ErbB2 stability and function by direct interaction.

Example 9

Erbin Expression is Associated with ErbB2-Overexpressing Breast Tumors

Figure 6A:
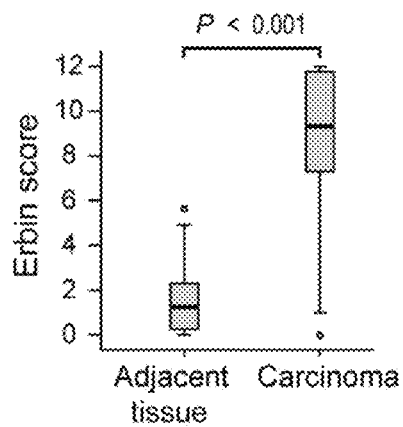
FIGS. 6A-6C show a correlation between Erbin and ErbB2 expression in human breast tumor tissues. (A) Increased Erbin levels in breast tumors. Erbin expression scores were shown as box plots, with horizontal lines indicating the median; the bottom and top of boxes indicating the 25$^{th}$ and 75$^{th}$ percentiles, respectively; and the vertical bars indicating the range of data. Outliers are marked with a circle. n=171, P<0.001, Kruskal-Wallis test with Pearson correction. (B) Correlation of Erbin expression with pathological grades of tumors. Erbin expression scores were shown as box plots, as described in [[b]] (B). Sample numbers of different grades are described below respective group. Data was analyzed by the Mann-Whitney U test. (C) Increased ErbB2 in tumor tissues with high levels of Erbin. Erbin expression levels were grouped into low, medium, or high levels as described in Experimental Procedures. ErbB2 expression scores were shown as box plots. Sample numbers of Erbin groups are described below perspective group. Data was analyzed by the Mann-Whitney U test.
Figure 6B:
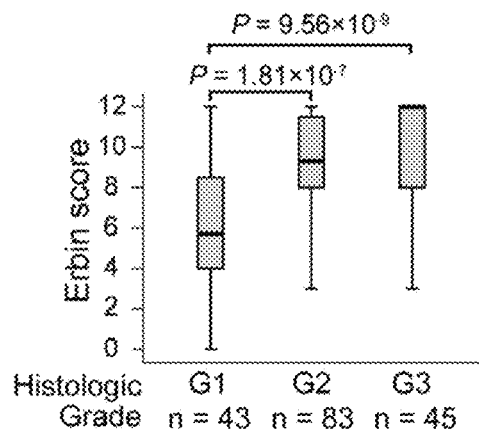
Figure 6C:
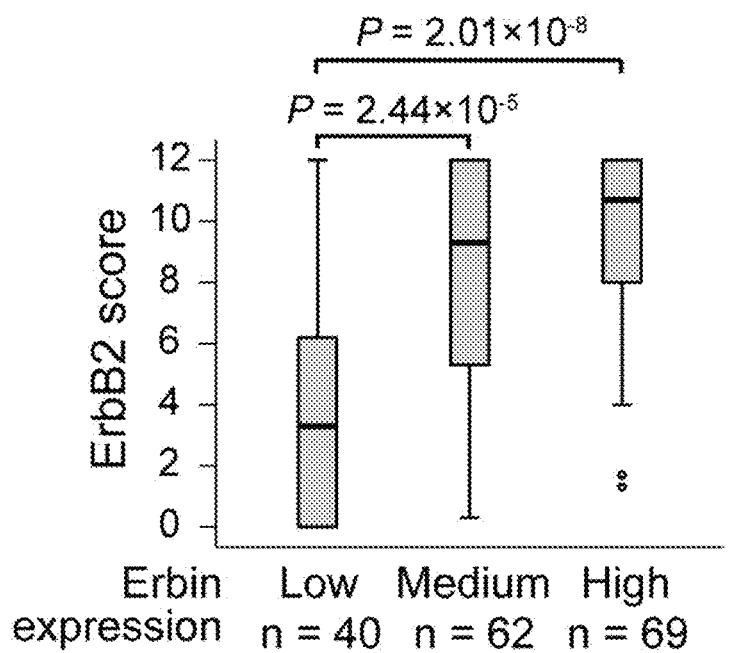
Figures 13A, 13B:
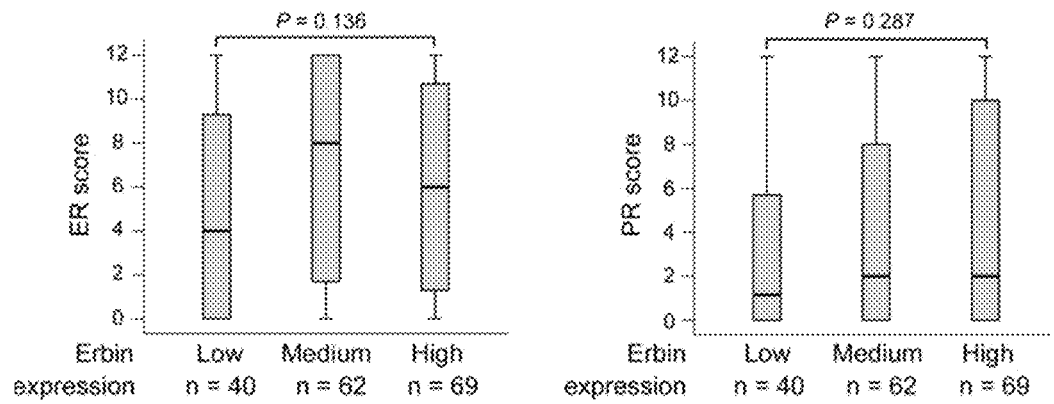
FIGS. 13A and 13B show scores of immunohistochemistry using specific anti-Erbin antibodies do not correlate with that of ER or PR. No correlation between Erbin expression and that of ER (A) or PR (B) in human breast cancers. Erbin expression levels were grouped into low, medium, or high levels as described in Experimental Procedures. ER or PR expression scores were shown as box plots, with horizontal lines indicating the median; the bottom and top of boxes indicating the 25$^{th}$ and 75$^{th}$ percentiles, respectively; and the vertical bars indicating the range of data. Data was analyzed by Kruskal-Wallis test with Pearson correction; P>0.05. Sample numbers of Erbin groups are described below perspective group.
Figure 14:
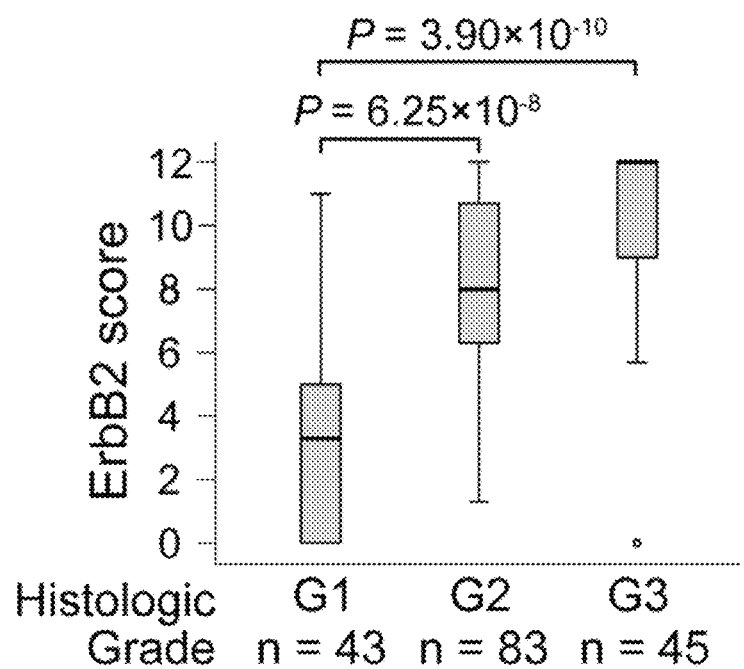
FIG. 14 shows the correlation of ErbB2 expression with pathological grades of tumors. ErbB2 expression scores were shown as box plots, as described in FIG. 6A. Sample numbers of different grades are described below respective group. Data was analyzed by the Mann-Whitney U test.

To determine if Erbin and ErbB2 expression correlates in primary breast tumor tissues, we examined Erbin expression in human breast samples and its relationship with ErbB2-overexpressing tumors. A total of 171 breast cancer specimens, mostly from invasive breast carcinomas, were analyzed by immunohistochemistry for ErbB2 and Erbin expression as well as estrogen receptor (ER) and progesterone receptor (PR) levels. Pre-absorption of the anti-Erbin antibody with the antigen reduced staining to background levels (data not shown), indicating its specificity. Compared to adjacent normal tissues, Erbin staining was significantly higher in tumor tissues (FIG. 6A). To gain better insight, Erbin staining was categorized to three levels (low, scores 0-4; medium, scores 5-8; and high, scores 9-12) by the German semi-quantitative scoring system that takes into consideration both staining intensity and area (Zaineddin, A. K., et al., *International journal of cancer*, 130:1401-1410, 2012; Remmele, W. et al., *Pathol. Res. Pract.*, 189, 862-866, 1993; Pan, X., et al., *Nature medicine*, 17, 708-714, 2011). Of 171 samples, 36% showed medium levels and 40% expressed high levels of Erbin (Table 2). Notably, there was a correlation between pathological grades and Erbin staining (FIG. 6B). Moreover, Erbin levels correlated with those of ErbB2 (FIG. 6C), but not that of ER or PR (FIGS. 13A and 13B). In agree with the associated function in tumor development, ErbB2 levels correlate with those of Erbin (Table 2) and pathological grades (FIG. 14). These observations demonstrate a strong association between Erbin and human breast cancer and ErbB2 expression in tumour samples.

TABLE 2

Association of Erbin levels with different clinicopathological characteristics, related to Figure 6.

| Characteristic | n | Erbin expression | | | P value |
| --- | --- | --- | --- | --- | --- |
| | | Low (40): n(%) | Medium (62): n(%) | High (69): n(%) | |
| Age, years | | | | | |
| Mean | 171 | 49.5 | 50.2 | 47.1 | 0.154 |
| 95% CI | | 46.1-52.8 | 48.0-52.5 | 44.9-49.4 | |
| Primary tumor size (cm) | | | | | |
| ≤2 | | 7  17.9% | 16  25.8% | 19  28.4% | |
| 2-5 | 168 | 25  64.1% | 40  64.5% | 41  61.2% | 0.620 |
| ≥5 | | 7  17.9% | 6  9.7% | 7  10.4% | |
| No. of positive nodes | | | | | |
| 0 | | 13  43.3% | 19  37.3% | 17  37.8% | |
| 1-3 | 126 | 9  30.0% | 15  29.4% | 16  35.6% | 0.867 |
| >3 | | 8  26.7% | 17  33.3% | 12  26.7% | |
| Histologic Grade | | | | | |
| G1 | | 22  55.0% | 17  27.4% | 4  5.8% | |
| G2 | 171 | 11  27.5% | 34  54.8% | 38  55.1% | $1.69 \times 10^{-7}$ ** |
| G3 | | 7  17.5% | 11  17.7% | 27  39.1% | |
| Estrogen receptor | | | | | |
| Low | | 20  50.0% | 24  38.7% | 29  42.0% | |
| Medium | 171 | 7  17.5% | 9  14.5% | 14  20.3% | 0.604 |
| High | | 13  32.5% | 29  46.8% | 26  37.7% | |
| Progesterone receptor | | | | | |
| Low | | 29  72.5% | 37  59.7% | 42  60.9% | |
| Medium | 171 | 6  15.0% | 11  17.7% | 9  13.0% | 0.493 |
| High | | 5  12.5% | 14  22.6% | 18  26.1% | |

TABLE 2-continued

Association of Erbin levels with different clinicopathological characteristics, related to Figure 6.

| Characteristic | n | Erbin expression | | | | | | P value |
|---|---|---|---|---|---|---|---|---|
| | | Low (40): n(%) | | Medium (62): n(%) | | High (69): n(%) | | |
| ErbB2/Neu status | | | | | | | | |
| Low | | 26 | 65.0% | 15 | 24.2% | 5 | 7.2% | |
| Medium | 171 | 9 | 22.5% | 14 | 22.6% | 19 | 27.5% | $7.08 \times 10^{-7}$ ** |
| High | | 5 | 12.5% | 33 | 53.2% | 45 | 65.2% | |

This cohort of 171 patients includes 158 cases of invasive ductal carcinoma (IDC), 6 cases of ductal carcinoma in situ (DCIS), 4 cases of invasive lobular carcinoma (ILC) and 3 cases of mixed type carcinoma. They were classified into grade I (G1, 43 cases), grade II (G2, 83 cases) and grade III (G3, 45 cases) based on an assessment of tubule/gland formation, nuclear pleomorphism and mitotic counts according to the WHO classification criteria (Elston, et al., *Histopathology*, 19:403-410, 1991; Robbins, 10 P., et al., *Hum Pathol*, 26:873-879, 1995; Ellis, I.O., et al., *World Health Organization Classification of Tumours*, p.14-4, 2003).
** $P < 0.001$.

Example 10

B2Tail Inhibits Breast Tumor Growth in Mice

Figure 7:
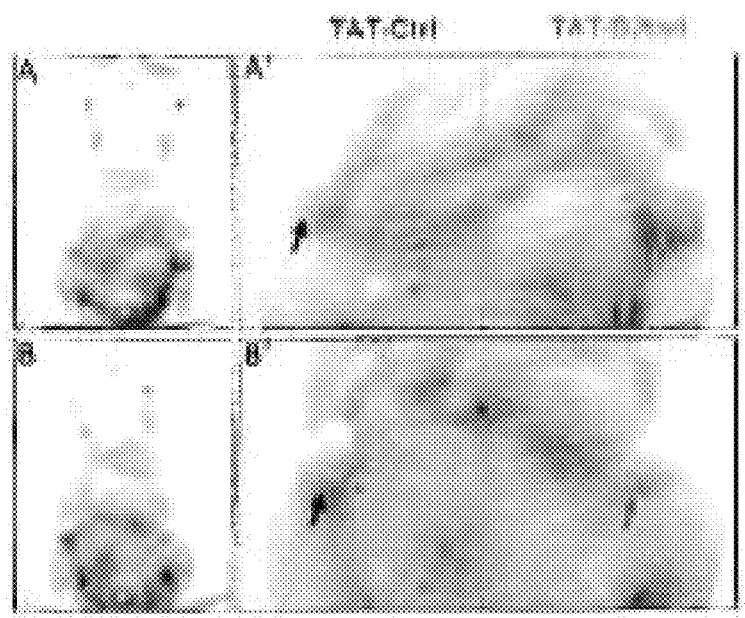
FIG. 7 is a microscopy image of a breast cancer tumor treated with Tat-ErbB2tail. TAT-ErbB2tail peptide inhibits breast tumor growth in nude mice. Human breast BT474 cancer cells (100 µl, 3.0×10$^5$ cells in 50% Matri-gel) were injected into fat pads of both sides of female mice. Resulting tumors were injected 2 weeks later with control (TAT-ctrl, left) or B2tail (TAT-B2tail, right) peptide (25 u.l, 5 mM), twice a week. Shown were representative images before injection (A, A') and one month after injection (B, B').

The results identify the ErbB2-Erbin interaction as a therapeutic target for fighting ErbB2-positive breast cancers. To test this, B2tail was tested for the ability to inhibit tumor growth in mice. Human breast BT474 cancer cells (100 ul, $3.0 \times 10^5$ cells in 50% Matri-gel) were injected into fat pads of both sides of virgin, female mice. Resulting tumors were injected 2 weeks later with control (TAT-Ctrl) or B2tail (TAT-B2tail) peptide (25 µl, 5 mM), twice a week[[.]]. Remarkably, the size of breast tumors in nude mice appeared to decrease after injection with B2tail (FIG. 7). These results demonstrate that the peptide B2tail is able to effectively suppress growth and progression of ErbB2-dependent tumors.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of treating ErbB2-dependent cancer comprising administering to a subject in need thereof an effective amount of the conjugate ErbB2 peptide of SEQ ID NO:2.

2. The method of claim 1, wherein the cancer is breast cancer.

3. A method of decreasing ErbB2-dependent growth of cancer cells comprising administering to a subject in need thereof an effective amount of the conjugate ErbB2 peptide of SEQ ID NO:2.

* * * * *

SEQUENCE LISTING

```
<160> NUMBER OF SEQ ID NOS: 15

<210> SEQ ID NO 1
<211> LENGTH: 15
<212> TYPE: PRT
<213> ORGANISM: Artificial Sequence
<220> FEATURE:
<223> OTHER INFORMATION: Peptide

<400> SEQUENCE: 1

Pro Thr Ala Glu Asn Pro Glu Tyr Leu Gly Leu Asp Val Pro Val
1               5                   10                  15

<210> SEQ ID NO 2
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 2

Tyr Gly Arg Lys Lys Arg Arg Gln Arg Arg Gly Pro Thr Ala Glu
1               5                   10                  15

Asn Pro Glu Tyr Leu Gly Leu Asp Val Pro Val
            20                  25

<210> SEQ ID NO 3
<211> LENGTH: 93
<212> TYPE: PRT
<213> ORGANISM: Artificial Sequence
<220> FEATURE:
```

<223> OTHER INFORMATION: PDZ domain

<400> SEQUENCE: 3

Ala Lys Gln Glu Ile Arg Val Arg Val Glu Lys Asp Pro Glu Leu Gly
1               5                   10                  15

Phe Ser Ile Ser Gly Gly Val Gly Gly Arg Gly Asn Pro Phe Arg Pro
            20                  25                  30

Asp Asp Asp Gly Ile Phe Val Thr Arg Val Gln Pro Glu Gly Pro Ala
        35                  40                  45

Ser Lys Leu Leu Gln Pro Gly Asp Lys Ile Ile Gln Ala Asn Gly Tyr
    50                  55                  60

Ser Phe Ile Asn Ile Glu His Gly Gln Ala Val Ser Leu Leu Lys Thr
65                  70                  75                  80

Phe Gln Asn Thr Val Glu Leu Ile Ile Val Arg Glu Val
                85                  90

<210> SEQ ID NO 4
<211> LENGTH: 11
<212> TYPE: PRT
<213> ORGANISM: Artificial Sequence
<220> FEATURE:
<223> OTHER INFORMATION: Antennapedia homeodomain

<400> SEQUENCE: 4

Tyr Gly Arg Lys Lys Arg Arg Gln Arg Arg Arg
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Basic domain TAT of HIV-1

<400> SEQUENCE: 5

Arg Lys Lys Arg Arg Gln Arg Arg Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Peptide

<400> SEQUENCE: 6

Arg Arg Arg Arg Arg Arg Arg
1               5

<210> SEQ ID NO 7
<211> LENGTH: 12
<212> TYPE: PRT
<213> ORGANISM: Artificial Sequence
<220> FEATURE:
<223> OTHER INFORMATION: Peptide

<400> SEQUENCE: 7

Arg Arg Gln Arg Arg Thr Ser Lys Leu Met Lys Arg
1               5                   10

<210> SEQ ID NO 8
<211> LENGTH: 27
<212> TYPE: PRT
<213> ORGANISM: Artificial Sequence

```
<220> FEATURE:
<223> OTHER INFORMATION: Peptide

<400> SEQUENCE: 8

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 9
<211> LENGTH: 29
<212> TYPE: PRT
<213> ORGANISM: Artificial Sequence
<220> FEATURE:
<223> OTHER INFORMATION: Peptide

<400> SEQUENCE: 9

Trp Glu Ala Lys Leu Ala Lys Ala Leu Ala Lys Ala Leu Ala Lys His
1               5                   10                  15

Leu Ala Lys Ala Leu Ala Lys Ala Leu Lys Cys Glu Ala
            20                  25

<210> SEQ ID NO 10
<211> LENGTH: 16
<212> TYPE: PRT
<213> ORGANISM: Artificial Sequence
<220> FEATURE:
<223> OTHER INFORMATION: Peptide

<400> SEQUENCE: 10

Arg Gln Ile Lys Ile Trp Phe Gln Asn Arg Arg Met Lys Trp Lys Lys
1               5                   10                  15

<210> SEQ ID NO 11
<211> LENGTH: 20
<212> TYPE: PRT
<213> ORGANISM: Artificial Sequence
<220> FEATURE:
<223> OTHER INFORMATION: Peptide

<400> SEQUENCE: 11

Gly Asp Ile Met Gly Glu Trp Gly Asn Glu Ile Phe Gly Ala Ile Ala
1               5                   10                  15

Gly Phe Leu Gly
            20

<210> SEQ ID NO 12
<211> LENGTH: 35
<212> TYPE: PRT
<213> ORGANISM: Artificial Sequence
<220> FEATURE:
<223> OTHER INFORMATION: Peptide

<400> SEQUENCE: 12

Arg Arg Arg Arg Arg Arg Arg Arg Arg Gly Glu Gly Asp Ile
1               5                   10                  15

Met Gly Glu Trp Gly Asn Glu Ile Phe Gly Ala Ile Ala Gly Phe Leu
            20                  25                  30

Gly Gly Glu
        35

<210> SEQ ID NO 13
<211> LENGTH: 11
<212> TYPE: PRT
```

```
<213> ORGANISM: Artificial Sequence
<220> FEATURE:
<223> OTHER INFORMATION: Synthetic Peptide

<400> SEQUENCE: 13

Tyr Gly Arg Lys Lys Arg Arg Gln Arg Arg
1               5                   10

<210> SEQ ID NO 14
<211> LENGTH: 59
<212> TYPE: DNA
<213> ORGANISM: Artificial Sequence
<220> FEATURE:
<223> OTHER INFORMATION: Synthetic Primer

<400> SEQUENCE: 14
tgcatccctc tagagaacaa ctttcaagag aagttgttct ctagagggat gcttttttc       59

<210> SEQ ID NO 15
<211> LENGTH: 63
<212> TYPE: DNA
<213> ORGANISM: Artificial Sequence
<220> FEATURE:
<223> OTHER INFORMATION: Synthetic Primer

<400> SEQUENCE: 15
tcgagaaaaa agcatccctc tagagaacaa cttctcttga aagttgttct ctagagggat      60
gca                                                                   63
```